(12) United States Patent
Podhajsky

(10) Patent No.: US 10,588,684 B2
(45) Date of Patent: Mar. 17, 2020

(54) HYDRAULIC CONDUCTIVITY MONITORING TO INITIATE TISSUE DIVISION

(75) Inventor: Ronald J. Podhajsky, Boulder, CO (US)

(73) Assignee: COVIDIEN LP, Mansfield, MA (US)

(*) Notice: Subject to any disclaimer, the term of this patent is extended or adjusted under 35 U.S.C. 154(b) by 1843 days.

(21) Appl. No.: 12/839,023

(22) Filed: Jul. 19, 2010

(65) Prior Publication Data

US 2012/0016359 A1 Jan. 19, 2012

(51) Int. Cl.
*A61B 18/12* (2006.01)
*A61B 18/00* (2006.01)

(52) U.S. Cl.
CPC ...... *A61B 18/1206* (2013.01); *A61B 18/1233* (2013.01); *A61B 2018/00636* (2013.01); *A61B 2018/00642* (2013.01); *A61B 2018/00702* (2013.01); *A61B 2018/00875* (2013.01)

(58) Field of Classification Search
CPC ............ A61B 18/1206; A61B 18/1233; A61B 2018/00636; A61B 2018/00642; A61B 2018/00702; A61B 2018/00875
USPC ........................................ 606/32, 34, 37–40
See application file for complete search history.

(56) References Cited

U.S. PATENT DOCUMENTS

| D263,020 S | 2/1982 | Rau, III |
| D295,893 S | 5/1988 | Sharkany et al. |
| D295,894 S | 5/1988 | Sharkany et al. |
| 4,934,365 A | 6/1990 | Morgenthaler |
| 5,167,658 A | 12/1992 | Ensslin |
| 5,496,312 A | 3/1996 | Klicek |

(Continued)

FOREIGN PATENT DOCUMENTS

| CN | 1103807 | 6/1995 |
| DE | 390937 | 3/1924 |

(Continued)

OTHER PUBLICATIONS

Alexander et al., "Magnetic Resonance Image-Directed Stereotactic Neurosurgery: Use of Image Fusion with Computerized Tomography to Enhance Spatial Accuracy" Journal Neurosurgery, 83 (1995), pp. 271-276.

(Continued)

*Primary Examiner* — Michael F Peffley
*Assistant Examiner* — Samantha M Good
(74) *Attorney, Agent, or Firm* — Carter, DeLuca & Farrell, LLP

(57) ABSTRACT

A method for performing an electrosurgical procedure at a surgical site on a patient includes continually sensing electrical and physical properties proximate the surgical site that includes acquiring readings of tissue electrical impedance with respect to time at the surgical site; identifying the minima and maxima of the impedance readings with respect to time; and correlating the minima and/or the maxima of the impedance readings with hydration level and/or hydraulic conductivity in the tissue at the surgical site. The method also includes controlling the application of electrosurgical energy to the surgical site to vary energy delivery based on the step of correlating the minima and/or the maxima of the impedance readings with the hydration level/or and the hydraulic conductivity in the tissue at the surgical site. The process may be an ablation process.

14 Claims, 5 Drawing Sheets

(56) References Cited

U.S. PATENT DOCUMENTS

| | | |
|---|---|---|
| 5,540,684 A | 7/1996 | Hassler, Jr. |
| 5,558,671 A | 9/1996 | Yates |
| 5,670,557 A | 9/1997 | Dietz et al. |
| 5,779,632 A | 7/1998 | Dietz et al. |
| 5,827,271 A | 10/1998 | Buysse et al. |
| 5,853,750 A | 12/1998 | Dietz et al. |
| 5,952,398 A | 9/1999 | Dietz et al. |
| 6,033,399 A | 3/2000 | Gines |
| D424,694 S | 5/2000 | Tetzlaff et al. |
| D425,201 S | 5/2000 | Tetzlaff et al. |
| 6,203,541 B1 | 3/2001 | Keppel |
| 6,210,403 B1 | 4/2001 | Klicek |
| 6,228,080 B1 | 5/2001 | Gines |
| D449,886 S | 10/2001 | Tetzlaff et al. |
| D457,958 S | 5/2002 | Dycus et al. |
| D457,959 S | 5/2002 | Tetzlaff et al. |
| 6,398,779 B1 | 6/2002 | Buysse et al. |
| 6,398,781 B1 | 6/2002 | Goble et al. |
| 6,575,969 B1 | 6/2003 | Rittman, III et al. |
| 6,633,234 B2 | 10/2003 | Wiener et al. |
| D496,997 S | 10/2004 | Dycus et al. |
| D499,181 S | 11/2004 | Dycus et al. |
| D525,361 S | 7/2006 | Hushka |
| D531,311 S | 10/2006 | Guerra et al. |
| 7,137,980 B2 | 11/2006 | Buysse et al. |
| D533,942 S | 12/2006 | Kerr et al. |
| D535,027 S | 1/2007 | James et al. |
| D541,418 S | 4/2007 | Schechter et al. |
| D541,938 S | 5/2007 | Kerr et al. |
| D564,662 S | 3/2008 | Moses et al. |
| RE40,388 E | 6/2008 | Gines |
| D613,412 S | 4/2010 | DeCarlo |
| 7,863,984 B1 | 1/2011 | Behnke |
| 7,963,785 B2 | 6/2011 | Arts et al. |
| 8,038,693 B2 | 10/2011 | Allen |
| 8,069,553 B2 | 12/2011 | Bonn |
| 8,118,808 B2 | 2/2012 | Smith et al. |
| 8,188,435 B2 | 5/2012 | Podhajsky et al. |
| 8,197,473 B2 | 6/2012 | Rossetto et al. |
| 8,202,270 B2 | 6/2012 | Rossetto et al. |
| 8,216,227 B2 | 7/2012 | Podhajsky |
| 8,235,981 B2 | 8/2012 | Prakash et al. |
| 8,282,632 B2 | 10/2012 | Rossetto |
| 8,292,881 B2 | 10/2012 | Brannan et al. |
| 8,328,799 B2 | 12/2012 | Brannan |
| 8,328,800 B2 | 12/2012 | Brannan |
| 8,328,801 B2 | 12/2012 | Brannan |
| 8,334,812 B2 | 12/2012 | Brannan |
| 8,343,145 B2 | 1/2013 | Brannan |
| 8,343,150 B2 | 1/2013 | Artale |
| 8,353,903 B2 | 1/2013 | Podhajsky |
| 8,355,803 B2 | 1/2013 | Bonn et al. |
| 8,382,750 B2 | 2/2013 | Brannan |
| 8,394,087 B2 | 3/2013 | Willyard et al. |
| 8,394,092 B2 | 3/2013 | Brannan |
| 8,409,187 B2 | 4/2013 | Bonn |
| 8,409,188 B2 | 4/2013 | Kim et al. |
| 8,430,871 B2 | 4/2013 | Brannan |
| 8,463,396 B2 | 6/2013 | Podhajsky |
| 8,469,953 B2 | 6/2013 | DeCarlo |
| 8,491,579 B2 | 7/2013 | Rossetto |
| 8,545,493 B2 | 10/2013 | Brannan et al. |
| 8,552,915 B2 | 10/2013 | Brannan |
| 8,556,889 B2 | 10/2013 | Brannan |
| 8,568,398 B2 | 10/2013 | Brannan |
| 8,568,401 B2 | 10/2013 | Brannan |
| 8,568,404 B2 | 10/2013 | Brannan |
| 8,617,153 B2 | 12/2013 | Lee et al. |
| 8,652,127 B2 | 2/2014 | Prakash et al. |
| 8,672,923 B2 | 3/2014 | Ladtkow et al. |
| 8,672,933 B2 | 3/2014 | Shiu et al. |
| 8,764,744 B2 | 7/2014 | Brannan |
| 8,777,939 B2 | 7/2014 | Lee et al. |
| 8,834,460 B2 | 9/2014 | Peterson |
| 8,876,814 B2 | 11/2014 | Bonn |
| 8,882,759 B2 | 11/2014 | Manley et al. |
| 8,906,007 B2 | 12/2014 | Bonn et al. |
| 8,968,288 B2 | 3/2015 | Brannan |
| 9,024,237 B2 | 5/2015 | Bonn |
| 9,028,474 B2 | 5/2015 | Brannan et al. |
| 9,031,668 B2 | 5/2015 | DeCarlo |
| 9,095,359 B2 | 8/2015 | Behnke, II et al. |
| 9,113,925 B2 | 8/2015 | Smith et al. |
| 9,113,926 B2 | 8/2015 | Brannan et al. |
| 9,113,927 B2 | 8/2015 | Kim et al. |
| 9,192,436 B2 | 11/2015 | Willyard et al. |
| 9,241,762 B2 | 1/2016 | Podhajsky et al. |
| 9,277,969 B2 | 3/2016 | Brannan et al. |
| 9,375,273 B2 | 6/2016 | Brannan et al. |
| 9,377,367 B2 | 6/2016 | Podhajsky et al. |
| 9,468,492 B2 | 10/2016 | Podhajsky et al. |
| 9,561,076 B2 | 2/2017 | Brannan et al. |
| 9,867,664 B2 | 1/2018 | Shiu et al. |
| 10,039,601 B2 | 8/2018 | Kim et al. |
| 10,045,819 B2 | 8/2018 | Jensen et al. |
| 2003/0004510 A1 | 1/2003 | Wham et al. |
| 2006/0064086 A1 | 3/2006 | Odom |
| 2007/0016274 A1* | 1/2007 | Boveja .............. A61B 18/1492 607/101 |
| 2007/0038209 A1 | 2/2007 | Buysse et al. |
| 2007/0173804 A1 | 7/2007 | Wham |
| 2007/0250052 A1 | 10/2007 | Wham |
| 2007/0282320 A1 | 12/2007 | Buysse |
| 2008/0015575 A1* | 1/2008 | Odom et al. ................. 606/51 |
| 2008/0114351 A1* | 5/2008 | Irisawa .............. A61B 18/1206 606/41 |
| 2010/0094275 A1 | 4/2010 | Wham |
| 2010/0268223 A1 | 10/2010 | Coe et al. |
| 2010/0268225 A1 | 10/2010 | Coe et al. |
| 2010/0331834 A1 | 12/2010 | Peterson et al. |
| 2011/0054458 A1 | 3/2011 | Behnke |
| 2011/0054459 A1 | 3/2011 | Peterson |
| 2011/0118731 A1 | 5/2011 | Ladtkow |
| 2011/0172659 A1 | 7/2011 | Brannan |
| 2011/0208180 A1 | 8/2011 | Brannan |
| 2011/0213353 A1 | 9/2011 | Lee et al. |
| 2011/0301589 A1 | 12/2011 | Podhajsky et al. |
| 2011/0319880 A1 | 12/2011 | Prakash et al. |

FOREIGN PATENT DOCUMENTS

| | | |
|---|---|---|
| DE | 1099658 | 2/1961 |
| DE | 1139927 | 11/1962 |
| DE | 1149832 | 6/1963 |
| DE | 1439302 | 1/1969 |
| DE | 2439587 | 2/1975 |
| DE | 2455174 | 5/1975 |
| DE | 2407559 | 8/1975 |
| DE | 2415263 | 10/1975 |
| DE | 2429021 | 1/1976 |
| DE | 2460481 | 6/1976 |
| DE | 2602517 | 7/1976 |
| DE | 2504280 | 8/1976 |
| DE | 2627679 | 1/1977 |
| DE | 2540968 | 3/1977 |
| DE | 2820908 | 11/1978 |
| DE | 2803275 | 8/1979 |
| DE | 2823291 | 11/1979 |
| DE | 2946728 | 5/1981 |
| DE | 3143421 | 5/1982 |
| DE | 3045996 | 7/1982 |
| DE | 3120102 | 12/1982 |
| DE | 3510586 | 10/1986 |
| DE | 3604823 | 8/1987 |
| DE | 8712328 | 3/1988 |
| DE | 3711511 | 6/1988 |
| DE | 3904558 | 8/1990 |
| DE | 3942998 | 7/1991 |
| DE | 4238263 | 5/1993 |
| DE | 4303882 | 8/1994 |
| DE | 4339049 | 5/1995 |
| DE | 29616210 | 1/1997 |
| DE | 19608716 | 4/1997 |
| DE | 19751106 | 5/1998 |

(56) References Cited

FOREIGN PATENT DOCUMENTS

| | | |
|---|---|---|
| DE | 19717411 | 11/1998 |
| DE | 19751108 | 5/1999 |
| DE | 19801173 | 7/1999 |
| DE | 19848540 | 5/2000 |
| DE | 10224154 | 12/2003 |
| DE | 10310765 | 9/2004 |
| DE | 10328514 | 3/2005 |
| DE | 102004022206 | 12/2005 |
| DE | 202005015147 | 3/2006 |
| EP | 0 246 350 | 11/1987 |
| EP | 0 521 264 | 1/1993 |
| EP | 0 556 705 | 8/1993 |
| EP | 0 558 429 | 9/1993 |
| EP | 0694291 | 1/1996 |
| EP | 0 836 868 | 4/1998 |
| EP | 0 882 955 | 12/1998 |
| EP | 1 034 748 | 9/2000 |
| EP | 1 159 926 | 5/2001 |
| EP | 1810634 | 7/2007 |
| EP | 1849425 | 10/2007 |
| EP | 1862137 | 12/2007 |
| FR | 179 607 | 11/1906 |
| FR | 1 275 415 | 10/1961 |
| FR | 1 347 865 | 11/1963 |
| FR | 2 235 669 | 1/1975 |
| FR | 2 276 027 | 1/1976 |
| FR | 2 313 708 | 12/1976 |
| FR | 2 502 935 | 10/1982 |
| FR | 2 517 953 | 6/1983 |
| FR | 2 573 301 | 5/1986 |
| FR | 2 862 813 | 5/2005 |
| FR | 2 864 439 | 7/2005 |
| JP | 5-5106 | 1/1993 |
| JP | 05-40112 | 2/1993 |
| JP | 06343644 | 12/1994 |
| JP | 07265328 | 10/1995 |
| JP | 08056955 | 3/1996 |
| JP | 08252263 | 10/1996 |
| JP | 09000492 | 1/1997 |
| JP | 09010223 | 1/1997 |
| JP | 11244298 | 9/1999 |
| JP | 2000342599 | 12/2000 |
| JP | 2000350732 | 12/2000 |
| JP | 2001008944 | 1/2001 |
| JP | 2001029356 | 2/2001 |
| JP | 2001128990 | 5/2001 |
| JP | 2001231870 | 8/2001 |
| JP | 2008142467 | 6/2008 |
| SU | 166452 | 11/1964 |
| SU | 401367 | 11/1974 |
| SU | 727201 | 4/1980 |
| WO | WO2010/035831 | 4/2010 |

OTHER PUBLICATIONS

Anderson et al., "A Numerical Study of Rapid Heating for High Temperature Radio Frequency Hyperthermia" International Journal of Bio-Medical Computing, 35 (1994), pp. 297-307.
Anonymous. (1999) Auto Suture MIBB Site Marker: Single Use Clip Applier, United States Surgical (Product instructions), 2 pages.
Anonymous. (2001) Disposable Chiba Biopsy Needles and Trays, Biopsy and Special Purpose Needles Cook Diagnostic and Interventional Products Catalog (products list), 4 pages.
Anonymous. (1987) Homer Mammalok™ Breast Lesion Needle/Wire Localizer, Namic® Angiographic Systems Division, Glens Falls, New York, (Hospital products price list), 4 pages.
Anonymous. (1999) MIBB Site Marker, United States Surgical (Sales brochure), 4 pages.
Anonymous. Blunt Tubes with Finished Ends. Pointed Cannula, Popper & Sons Biomedical Instrument Division, (Products Price List), one page, Jul. 19, 2000.
Anonymous. Ground Cannulae, ISPG, New Milford, CT, (Advertisement) one page, Jul. 19, 2000.

B. Levy M.D. et al., "Randomized Trial of Suture Versus Electrosurgical Bipolar Vessel Sealing in Vaginal Hysterectomy" Obstetrics & Gynecology, vol. 102, No. 1, Jul. 2003.
B. Levy M.D. et al., "Update on Hysterectomy New Technologies and Techniques" OBG Management, Feb. 2003.
B. Levy M.D., "Use of a New Vessel Ligation Device During Vaginal Hysterectomy" FIGO 2000, Washington, D.C.
B. F. Mullan et al., (May 1999) "Lung Nodules: Improved Wire for CT-Guided Localization," Radiology 211:561-565.
B. T. Heniford M.D. et al., "Initial Research and Clinical Results with an Electrothermal Bipolar Vessel Sealer" Oct. 1999.
Bergdahl et al., "Studies on Coagulation and the Development of an Automatic Computerized Bipolar Coagulator" Journal of Neurosurgery 75:1 (Jul. 1991), pp. 148-151.
Bulletin of the American Physical Society, vol. 47, No. 5, Aug. 2002, p. 41.
C. F. Gottlieb et al., "Interstitial Microwave Hyperthermia Applicators having Submillimetre Diameters", Int. J. Hyperthermia, vol. 6, No. 3, pp. 707-714, 1990.
C. H. Durney et al., "Antennas for Medical Applications", Antenna Handbook: Theory Application and Design, p. 24-40, Van Nostrand Reinhold, 1988 New York, V.T. Lo, S.W. Lee.
Carbonell et al., "Comparison of the Gyrus PlasmaKinetic Sealer and the Valleylab LigaSure™ Device in the Hemostasis of Small, Medium, and Large-Sized Arteries" Carolinas Laparoscopic and Advanced Surgery Program, Carolinas Medical Center, Charlotte, NC 2003.
Carus et al., "Initial Experience With the LigaSure™ Vessel Sealing System in Abdominal Surgery" Innovations That Work, Jun. 2002.
Chicharo et al., "A Sliding Goertzel Algorithm" Aug. 1996 DOS pp. 283-297 Signal Processing, Elsevier Science Publishers B.V. Amsterdam, NL, vol. 52, No. 3.
Chou, C.K., (1995) "Radiofrequency Hyperthermia in Cancer Therapy," Chapter 941n Biologic Effects of Nonionizing Electromagnetic Fields, CRC Press, Inc., pp. 1424-1428.
Chung et al., "Clinical Experience of Sutureless Closed Hemorrhoidectomy with LigaSure™" Diseases of the Colon & Rectum, vol. 46, No. 1, Jan. 2003.
Cosman et al., "Methods of Making Nervous System Lesions" In William RH, Rengachary SS (eds): Neurosurgery, New York: McGraw•Hill, vol. 111, (1984), pp. 2490-2499.
Cosman et al., "Radiofrequency Lesion Generation and its Effect on Tissue Impedence", Applied Neurophysiology, 51:230-242, 1988.
Cosman et al., "Theoretical Aspects of Radiofrequency Lesions in the Dorsal Root Entry Zone" Neurosurgery 15:(1984), pp. 945-950.
Crawford et al., "Use of the LigaSure™ Vessel Sealing System in Urologic Cancer Surger" Grand Rounds in Urology 1999, vol. 1, Issue 4, pp. 10-17.
Dulemba et al., "Use of a Bipolar Electrothermal Vessel Sealer in Laparoscopically Assisted Vaginal Hysterectomy" Sales/Product Literature; Jan. 2004.
E. David Crawford, "Evaluation of a New Vessel Sealing Device in Urologic Cancer Surgery" Sales/Product Literature 2000.
E. David Crawford, "Use of a Novel Vessel Sealing Technology in Management of the Dorsal Veinous Complex" Sales/Product Literature 2000.
Esterline, "Light Key Projection Keyboard" 2004 Advanced Input Systems, located at: <http://www.advanced-input.com/lightkey> last visited on Feb. 10, 2005.
Esterline Product Literature, "Light Key: Visualize a Virtual Keyboard. One With No Moving Parts", Nov. 1, 2003; 4 pages.
Geddes et al., "The Measurement of Physiologic Events by Electrical Impedance" Am. J. MI, Jan. Mar. 1964, pp. 16-27.
Goldberg et al., "Image-guided Radiofrequency Tumor Ablation: Challenges and Opportunities—Part I", (2001) J Vasc. Interv. Radiol, vol. 12, pp. 1021-1032.
Goldberg et al. (1995) "Saline-enhanced RF Ablation: Demonstration of Efficacy and Optimization of Parameters", Radiology, 197(P): 140 (Abstr).
Goldberg et al., "Tissue Ablation with Radiofrequency: Effect of Probe Size, Gauge, Duration, and Temperature on Lesion Volume" Acad Radio (1995) vol. 2, No. 5, pp. 399-404.

(56) References Cited

OTHER PUBLICATIONS

H. Schwarzmaier et al., "Magnetic Resonance Imaging of Microwave Induced Tissue Heating" Dept. of Laser Medicine & Dept. of Diagnostic Radiology; Heinrich-Heine-University, Duesseldorf, Germany; Dec. 8, 1994; pp. 729-731.
Heniford et al., "Initial Results with an Electrothermal Bipolar Vessel Sealer" Surgical Endoscopy (2001) 15:799-801.
Herman at al., "Laparoscopic Intestinal Resection With the LigaSure™ Vessel Sealing System: A Case Report" Innovations That Work, Feb. 2002.
Humphries Jr. et al., "Finite•Element Codes to Model Electrical Heating and Non•Llnear Thermal Transport in Biological Media", Proc. ASME HTD-355, 131 (1997).
Ian D. McRury et al., The Effect of Ablation Sequence and Duration on Lesion Shape Using Rapidly Pulsed Radiofrequency Energy Through Electrodes, Feb. 2000, Springer Netherlands, vol. 4; No. 1, pp. 307-320.
Jarrett et al., "Use of the LigaSure™ Vessel Sealing System for Peri-Hilar Vessels in Laparoscopic Nephrectomy" Sales/Product Literature 2000.
Johnson et al., "Evaluation of a Bipolar Electrothermal Vessel Sealing Device in Hemorrhoidectomy" Sales/Product Literature, Jan. 2004.
Johnson, "Evaluation of the LigaSure™ Vessel Sealing System in Hemorrhoidectormy" American College of Surgeons (ACS) Clinic La Congress Poster (2000).
Johnson et al., "New Low-Profile Applicators for Local Heating of Tissues", IEEE Transactions on Biomedical Engineering, vol. BME-31, No. 1, Jan. 1984, pp. 28-37.
Johnson, "Use of the LigaSure™ Vessel Sealing System in Bloodless Hemorrhoidectomy" Innovations That Work, Mar. 2000.
Joseph G. Andriole M.D. et al., "Biopsy Needle Characteristics Assessed in the Laboratory", Radiology 148: 659-662, Sep. 1983.
Joseph Ortenberg, "LigaSure™ System Used in Laparoscopic 1st and 2nd Stage Orchiopexy" Innovations That Work, Nov. 2002.
K. Ogata, Modern Control Engineering, Prentice-Hall, Englewood Cliffs, N.J., 1970.
Kennedy et al., "High-burst-strength, feedback-controlled bipolar vessel sealing" Surgical Endoscopy (1998) 12: 876-878.
Kopans, D.B. et al., (Nov. 1985) "Spring Hookwire Breast Lesion Localizer: Use with Rigid-Compression. Mammographic Systems," Radiology 157(2):537-538.
Koyle et al., "Laparoscopic Palomo Varicocele Ligation in Children and Adolescents" Pediatric Endosurgery & Innovative Techniques, vol. 6, No. 1, 2002.
LigaSure™ Vessel Sealing System, the Seal of Confidence in General, Gynecologic, Urologic, and Laparaoscopic Surgery, Sales/Product Literature, Jan. 2004.
Livraghi et al., (1995) "Saline-enhanced RF Tissue Ablation in the Treatment of Liver Metastases", Radiology, p. 140 (Abstr).
Lyndon B. Johnson Space Center, Houston, Texas, "Compact Directional Microwave Antenna for Localized Heating," NASA Tech Briefs, Mar. 2008.
M. A. Astrahan, "A Localized Current Field Hyperthermia System for Use with 192-Iridium Interstitial Implants" Medical Physics. 9(3), May/Jun. 1982.
Magdy F. Iskander et al., "Design Optimization of Interstitial Antennas", IEEE Transactions on Biomedical Engineering, vol. 36, No. 2, Feb. 1989, pp. 238-246.
McGahan et al., (1995) "Percutaneous Ultrasound-guided Radiofrequency Electrocautery Ablation of Prostate Tissue in Dogs", Acad Radiol, vol. 2, No. 1: pp. 61-65.
McLellan et al., "Vessel Sealing for Hemostasis During Pelvic Surgery" Int'l Federation of Gynecology and Obstetrics FIGO World Congress 2000, Washington, DC.
MDTECH product literature (Dec. 1999) "FlexStrand": product description, 1 page.
MDTECH product literature (Mar. 2000) I'D Wire: product description, 1 page.
Medtrex Brochure "The O.R. Pro 300" 1 page, Sep. 1998.

Michael Choti, "Abdominoperineal Resection with the LigaSure™ Vessel Sealing System and LigaSure™ Atlas 20 cm Open Instrument" Innovations That Work, Jun. 2003.
Muller et al., "Extended Left Hemicolectomy Using the LigaSure™ Vessel Sealing System" Innovations That Work. LJ, Sep. 1999.
Murakami, R. et al., (1995). "Treatment of Hepatocellular Carcinoma: Value of Percutaneous Microwave Coagulation," American Journal of Radiology (AJR) 164:1159-1164.
Ni Wei et al., "A Signal Processing Method for the Coriolis Mass Flowmeter Based on a Normalized . . . " Journal of Applied Sciences•Yingyong Kexue Xuebao, Shangha CN, vol. 23, No. 2:(Mar. 2005); pp. 160-184.
Ogden, "Goertzel Alternative to the Fourier Transform" Jun. 1993 pp. 485-487 Electronics World; Reed Business Publishing, Sutton, Surrey, BG, vol. 99, No. 9, 1687.
Olsson M.D. et al., "Radical Cystectomy in Females" Current Surgical Techniques in Urology, vol. 14, Issue 3, 2001.
Organ, L W., "Electrophysiologic Principles of Radiofrequency Lesion Making" Appl. Neurophysiol, vol. 39: pp. 69-76 (1976/77).
P.R. Stauffer et al., "Interstitial Heating Technologies", Thermoradiotheray and Thermochemotherapy (1995) vol. I, Biology, Physiology, Physics, pp. 279-320.
Palazzo et al., "Randomized clinical trial of LigaSure™ versus open haemorrhoidectomy" British Journal of Surgery 2002,89,154-157
"Innovations in Electrosurgery" Sales/Product Literature; Dec. 31, 2000.
Paul G. Horgan, "A Novel Technique for Parenchymal Division During Hepatectomy" The American Journal of Surgery, vol. 181, No. 3, Apr. 2001, pp. 236-237.
Peterson et al., "Comparison of Healing Process Following Ligation with Sutures and Bipolar Vessel Sealing" Surgical Technology International (2001).
R. Gennari et al., (Jun. 2000) "Use of Technetium-99m-Labeled Colloid Albumin for Preoperative and Intraoperative Localization of Non palpable Breast Lesions," American College of Surgeons. 190(6):692-699.
Valleylab Brochure, "Reducing Needlestick Injuries in the Operating Room" 1 page, Mar. 2001.
Reidenbach, (1995) "First Experimental Results with Special Applicators for High-Frequency Interstitial Thermotherapy", Society Minimally Invasive Therapy, 4(Suppl 1):40 (Abstr).
Richard Wolf Medical Instruments Corp. Brochure, "Kleppinger Bipolar Forceps & Bipolar Generator" 3 pages, Jan. 1989.
Rothenberg et al., "Use of the LigaSure™ Vessel Sealing System in Minimally Invasive Surgery in Children" Int'l Pediatric Endosurgery Group (I PEG) 2000.
Sayfan et al., "Sutureless Closed Hemorrhoidectomy: A New Technique" Annals of Surgery, vol. 234, No. 1, Jul. 2001, pp. 21-24.
Sengupta et al., "Use of a Computer-Controlled Bipolar Diathermy System in Radical Prostatectomies and Other Open Urological Surgery" ANZ Journal of Surgery (2001) 71.9 pp. 538-540.
Sigel et al., "The Mechanism of Blood Vessel Closure by High Frequency Electrocoagulation" Surgery Gynecology & Obstetrics, Oct. 1965 pp. 823-831.
Solbiati et al., (2001) "Percutaneous Radio-frequency Ablation of Hepatic Metastases from Colorectal Cancer: Long-term Results in 117 Patients", Radiology, vol. 221, pp. 159-166.
Solbiati et al. (1995) "Percutaneous US-guided RF Tissue Ablation of Liver Metastases: Long-term Follow-up", Radiology, pp. 195-203.
Strasberg et al., "Use of a Bipolar Vassel-Sealing Device for Parenchymal Transection During Liver Surgery" Journal of Gastrointestinal Surgery, vol. 6, No. 4, Jul./Aug. 2002 pp. 569-574.
Stuart W. Young, Nuclear Magnetic Resonance Imaging—Basic Principles, Raven Press, New York, 1984.
Sugita et al., "Bipolar Coagulator with Automatic Thermocontrol" J. Neurosurg., vol. 41, Dec. 1944, pp. 777-779.
Sylvain Labonte et al., "Monopole Antennas for Microwave Catheter Ablation", IEEE Trans. on Microwave Theory and Techniques, vol. 44, No. 10, pp. 1832-1840, Oct. 1995.
T. Matsukawa et al., "Percutaneous Microwave Coagulation Therapy in Liver Tumors", Acta Radiologica, vol. 38, pp. 410-415, 1997.

(56) References Cited

OTHER PUBLICATIONS

T. Seki et al., (1994) "Ultrasonically Guided Percutaneous Microwave Coagulation Therapy for Small Hepatocellular Carcinoma," Cancer 74(3):817-825.
Urologix, Inc.—Medical Professionals: Targis™ Technology (Date Unknown). "Overcoming the Challenge" located at: <http://www.urologix.com!medicaUtechnology.html > last visited on Apr. 27, 2001, 3 pages.
Urrutia et al., (1988). "Retractable-Barb Needle for Breast Lesion Localization: Use in 60 Cases," Radiology 169(3):845-847.
Valleylab Brochure, "Valleylab Electroshield Monitoring System" 2 pages, Nov. 1995.
ValleyLab Brochure, "Electosurgery: A Historical Overview", Innovations in Electrosurgery, 1999.
Vallfors et al., "Automatically Controlled Bipolar Electrocoagulation—'COA-COMP'" Neurosurgical Review 7:2-3 (1984) pp. 187-190.
W. Scott Helton, "LigaSure™ Vessel Sealing System: Revolutionary Hemostasis Product for General Surgery" Sales/Product Literature 1999.
Wald et al., "Accidental Burns", JAMA, Aug. 16, 1971, vol. 217, No. 7, pp. 916-921.
Walt Boyles, "Instrumentation Reference Book", 2002, Butterworth-Heinemann, pp. 262-264.
Wonnell et al., "Evaluation of Microwave and Radio Frequency Catheter Ablation in a Myocardium-Equivalent Phantom Model", IEEE Transactions on Biomedical Engineering, vol. 39, No. 10, Oct. 1992; pp. 1086-1095.
European Search Report EP 98300964.8 dated Dec. 13, 2000.
European Search Report EP 98944778 dated Nov. 7, 2000.
European Search Report EP 98958575.7 dated Oct. 29, 2002.
European Search Report EP 02786604.5 dated Feb. 10, 2010.
European Search Report EP 03721482 dated Feb. 6, 2006.
European Search Report EP 04009964 dated Jul. 28, 2004.
European Search Report EP 04013772 dated Apr. 11, 2005.
European Search Report EP 04015980 dated Nov. 3, 2004.
European Search Report EP 04015981.6 dated Oct. 25, 2004.
European Search Report EP 04027314 dated Mar. 31, 2005.
European Search Report EP 04027479 dated Mar. 17, 2005.
European Search Report EP 04027705 dated Feb. 10, 2005.
European Search Report EP 04710258 dated Oct. 15, 2004.
European Search Report EP 04752343.6 dated Jul. 31, 2007.
European Search Report EP 04778192.7 dated Jul. 1, 2009.
European Search Report EP 05002027.0 dated May 12, 2005.
European Search Report EP 05002769.7 dated Jun. 19, 2006.
European Search Report EP 05013463.4 dated Oct. 7, 2005.
European Search Report EP 05013895 dated Oct. 21, 2005.
European Search Report EP 05014156.3 dated Jan. 4, 2006.
European Search Report EP 05016399 dated Jan. 13, 2006.
European Search Report EP 05017281 dated Nov. 24, 2005.
European Search Report EP 05019130.3 dated Oct. 27, 2005.
European Search Report EP 05019882 dated Feb. 16, 2006.
European Search Report EP 05020665.5 dated Feb. 27, 2006.
European Search Report EP 05020666.3 dated Feb. 27, 2006.
European Search Report EP 05021025.1 dated Mar. 13, 2006.
European Search Report EP 05021197.8 dated Feb. 20, 2006.
European Search Report EP 05021777 dated Feb. 23, 2006.
European Search Report EP 05021779.3 dated Feb. 2, 2006.
European Search Report EP 05021780.1 dated Feb. 23, 2006.
European Search Report EP 05021935 dated Jan. 27, 2006.
European Search Report EP 05021936.9 dated Feb. 6, 2006.
European Search Report EP 05021937.7 dated Jan. 23, 2006.
European Search Report EP 05021939 dated Jan. 27, 2006.
European Search Report EP 05021944.3 dated Jan. 25, 2006.
European Search Report EP 05022350.2 dated Jan. 30, 2006.
European Search Report EP 05023017.6 dated Feb. 24, 2006.
European Search Report EP 05025423.4 dated Jan. 19, 2007.
European Search Report EP 05025424 dated Jan. 30, 2007.
European Search Report EP 05810523 dated Jan. 29, 2009.
European Search Report EP 06000708.5 dated May 15, 2006.
European Search Report EP 06002279.5 dated Mar. 30, 2006.
European Search Report EP 06005185.1 dated May 10, 2006.
European Search Report EP 06005540 dated Sep. 24, 2007.
European Search Report EP 06006717.0 dated Aug. 11, 2006.
European Search Report EP 06006961 dated Oct. 22, 2007.
European Search Report EP 06006963 dated Aug. 4, 2006.
European Search Report EP 06008779.8 dated Jul. 13, 2006.
European Search Report EP 06009435 dated Jul. 13, 2006.
European Search Report EP 06010499.9 dated Jan. 29, 2008.
European Search Report EP 06014461.5 dated Oct. 31, 2006.
European Search Report EP 06018206.0 dated Oct. 20, 2006.
European Search Report EP 06019768 dated Jan. 17, 2007.
European Search Report EP 06020574.7 dated Oct. 2, 2007.
European Search Report EP 06020583.8 dated Feb. 7, 2007.
European Search Report EP 06020584.6 dated Feb. 1, 2007.
European Search Report EP 06020756.0 dated Feb. 16, 2007.
European Search Report EP 06022028.2 dated Feb. 13, 2007.
European Search Report EP 06023756.7 dated Feb. 21, 2008.
European Search Report EP 06024122.1 dated Apr. 16, 2007.
European Search Report EP 06024123.9 dated Mar. 6, 2007.
European Search Report EP 06025700.3 dated Apr. 12, 2007.
European Search Report EP 07000885.9 dated May 15, 2007.
European Search Report EP 07001480.8 dated Apr. 19, 2007.
European Search Report EP 07001481.6 dated May 2, 2007.
European Search Report EP 07001485.7 dated May 23, 2007.
European Search Report EP 07001488.1 dated Jun. 5, 2007.
European Search Report EP 07001489.9 dated Dec. 20, 2007.
European Search Report EP 07001491 dated Jun. 6, 2007.
European Search Report EP 07001527.6 dated May 18, 2007.
European Search Report EP 07007783.9 dated Aug. 14, 2007.
European Search Report EP 07008207.8 dated Sep. 13, 2007.
European Search Report EP 07009026.1 dated Oct. 8, 2007.
European Search Report EP 07009028 dated Jul. 16, 2007.
European Search Report EP 07009029.5 dated Jul. 20, 2007.
European Search Report EP 07009321.6 dated Aug. 28, 2007.
European Search Report EP 07009322.4 dated Jan. 14, 2008.
European Search Report EP 07010672.9 dated Oct. 16, 2007.
European Search Report EP 07010673.7 dated Oct. 5, 2007.
European Search Report EP 07013779.9 dated Oct. 26, 2007.
European Search Report EP 07015191.5 dated Jan. 23, 2008.
European Search Report EP 07015601.3 dated Jan. 4, 2008.
European Search Report EP 07015602.1 dated Dec. 20, 2007.
European Search Report EP 07018375.1 dated Jan. 8, 2008.
European Search Report EP 07018821 dated Jan. 14, 2008.
European Search Report EP 07019173.9 dated Feb. 12, 2008.
European Search Report EP 07019174.7 dated Jan. 29, 2008.
European Search Report EP 07019178.8 dated Feb. 12, 2008.
European Search Report EP 07020283.3 dated Feb. 5, 2008.
European Search Report EP 07253835.8 dated Dec. 20, 2007.
European Search Report EP 08001019 dated Sep. 23, 2008.
European Search Report EP 08004975 dated Jul. 24, 2008.
European Search Report EP 08006731.7 dated Jul. 29, 2008.
European Search Report EP 08006733 dated Jul. 7, 2008.
European Search Report EP 08006734.1 dated Aug. 18, 2008.
European Search Report EP 08006735.8 dated Jan. 8, 2009.
European Search Report EP 08011282 dated Aug. 14, 2009.
European Search Report EP 08011705 dated Aug. 20, 2009.
European Search Report EP 08011705.4 extended dated Nov. 4, 2009.
European Search Report EP 08012829.1 dated Oct. 29, 2008.
European Search Report EP 08015842 dated Dec. 5, 2008.
European Search Report EP 08019920.1 dated Mar. 27, 2009.
European Search Report EP 08020530.5 dated May 27, 2009.
European Search Report EP 08169973.8 dated Apr. 6, 2009.
European Search Report EP 09010873.9 extended dated Nov. 13, 2009.
European Search Report EP 09010877.0 extended dated Dec. 3, 2009.
European Search Report EP 09151621 dated Jun. 18, 2009.
European Search Report EP 09156861.8 dated Aug. 4, 2009.
European Search Report EP 09161502.1 dated Sep. 2, 2009.
European Search Report EP 09161502.1 extended dated Oct. 30, 2009.

(56) References Cited

OTHER PUBLICATIONS

European Search Report EP 09165976.3 extended dated Mar. 17, 2010.
European Search Report EP 09166708 dated Oct. 15, 2009.
European Search Report EP 09166708.9 dated Mar. 18, 2010.
European Search Report EP 09169376.2 extended dated Dec. 16, 2009.
European Search Report EP 09172188.6 extended dated Apr. 23, 2010.
European Search Report EP 09172838.6 extended dated Jan. 20, 2010.
European Search Report EP 09173268.5 extended dated Jan. 27, 2010.
European Search Report EP 10158944.8 extended dated Jun. 21, 2010.
European Search Report EP 10161722.3 extended dated Jun. 16, 2010.
International Search Report PCT/US98/18640 dated Jan. 29, 1999.
International Search Report PCT/US98/23950 dated Jan. 14, 1999.
International Search Report PCT/US99/24869 dated Feb. 11, 2000.
International Search Report PCT/US01/11218 dated Aug. 14, 2001.
International Search Report PCT/US01/11224 dated Nov. 13, 2001.
International Search Report PCT/US01/11340 dated Aug. 16, 2001.
International Search Report PCT/US01/11420 dated Oct. 16, 2001.
International Search Report PCT/US02/01890 dated Jul. 25, 2002.
International Search Report PCT/US02/11100 dated Jul. 16, 2002.
International Search Report PCT/US03/09483 dated Aug. 13, 2003.
International Search Report PCT/US03/22900 dated Dec. 2, 2003.
International Search Report PCT/US03/37110 dated Jul. 25, 2005.
International Search Report PCT/US03/37111 dated Jul. 28, 2004.
International Search Report PCT/US03/37310 dated Aug. 13, 2004.
International Search Report PCT/US04/04685 dated Aug. 27, 2004.
International Search Report PCT/US04/13273 dated Dec. 15, 2004.
International Search Report PCT/US04/15311 dated Jan. 12, 2005.
International Search Report PCT/US05/36168 dated Aug. 28, 2006.
International Search Report PCT/US08/052460 dated Apr. 24, 2008.
International Search Report PCT/US09/31658 dated Mar. 11, 2009.
European Search Report for European Application No. 11174318.3 dated Nov. 7, 2011.
U.S. Appl. No. 08/136,098 to Roger A. Stem, filed Oct. 14, 1993, abandoned.

* cited by examiner

HYDRAULIC CONDUCTIVITY MONITORING TO INITIATE TISSUE DIVISION

BACKGROUND

1. Technical Field

This application relates to electrosurgical surgery and, in particular, to control systems for electrosurgical generators and to methods of determining tissue moisture content during use of electrosurgical instruments.

2. Description of Related Art

Electrosurgical generators are employed by surgeons in conjunction with an electrosurgical instrument to cut, coagulate, desiccate and/or seal patient tissue. High frequency electrical energy, e.g., radio frequency (RF) energy, is produced by the electrosurgical generator and applied to the tissue by the electrosurgical tool. Both monopolar and bipolar configurations are commonly used during electrosurgical procedures.

Electrosurgical techniques and instruments can be used to coagulate small diameter blood vessels or to seal large diameter vessels or tissue, e.g., soft tissue structures, such as lung, brain and intestine. A surgeon can either cauterize, coagulate/desiccate and/or simply reduce or slow bleeding, by controlling the intensity, frequency and duration of the electrosurgical energy applied between the electrodes and through the tissue. For the purposes herein, the term "cauterization" is defined as the use of heat to destroy tissue (also called "diathermy" or "electrodiathermy"). The term "coagulation" is defined as a process of desiccating tissue wherein the tissue cells are ruptured and dried. "Vessel sealing" is defined as the process of liquefying the collagen and elastin in the tissue so that it reforms into a fused mass with significantly-reduced demarcation between the opposing tissue structures (opposing walls of the lumen). Coagulation of small vessels is usually sufficient to permanently close them. Larger vessels or tissue need to be sealed to assure permanent closure.

In order to achieve one of the above desired surgical effects without causing unwanted charring of tissue at the surgical site or causing collateral damage to adjacent tissue, e.g., thermal spread, it is necessary to control the output from the electrosurgical generator, e.g., power, waveform, voltage, current, pulse rate, etc.

It is known that measuring the electrical impedance and change thereof across the tissue at the surgical site provides a good indication of the state of desiccation or drying of the tissue, e.g., as the tissue dries or loses moisture, the impedance across the tissue rises. This observation has been utilized in some electrosurgical generators to regulate the electrosurgical power based on a measurement of tissue impedance. For example, commonly owned U.S. Pat. No. 6,210,403 relates to a system and method for automatically measuring the tissue impedance and altering the output of the electrosurgical generator based on the measured impedance across the tissue. The entire contents of this patent is hereby incorporated by reference herein.

It has been determined that the particular waveform of electrosurgical energy can be tailored to enhance a desired surgical effect, e.g., cutting, coagulation, sealing, blend, etc. For example, the "cutting" mode typically entails generating an uninterrupted sinusoidal waveform in the frequency range of 100 kHz to 4 MHz with a crest factor in the range of 1.4 to 2.0. The "blend" mode typically entails generating an uninterrupted cut waveform with a duty cycle in the range of 25% to 75% and a crest factor in the range of 2.0 to 5.0. The "coagulate" mode typically entails generating an uninterrupted waveform with a duty cycle of approximately 10% or less and a crest factor in the range of 5.0 to 12.0. In order to effectively and consistently seal vessels or tissue, a pulse-like waveform may be employed. Energy may be supplied in a continuous fashion to seal vessels in tissue if the energy input/output is responsive to tissue hydration/volume through feedback control. Delivery of the electrosurgical energy in pulses allows the tissue to cool down and also allows some moisture to return to the tissue between pulses which are both known to enhance the sealing process.

It is further known to clamp or clip excess voltage output from the electrosurgical generator by the use of avalanche devices, such as diodes, zener diodes and transorbs, resulting in absorption and dissipation of excess energy in the form of heat.

Commonly owned U.S. Pat. No. 6,398,779 discloses a sensor which measures the initial tissue impedance with a calibrating pulse which, in turn, sets various electrical parameters based on a look-up table stored in a computer database. The transient pulse width associated with each pulse measured during activation is used to set the duty cycle and amplitude of the next pulse. Generation of electrosurgical power is automatically terminated based on a predetermined value of the tissue impedance across the tissue.

Commonly owned U.S. Patent Application Publication US 2007/0038209 A1 by Buysse et al., "METHOD AND SYSTEM FOR CONTROLLING OUTPUT OF RF MEDICAL GENERATOR", the entire contents of which is incorporated by reference herein, discloses a sensor module for sensing (measuring) tissue moisture (which is often indicative of tissue type) and generating a moisture content value and/or determining tissue type. Moisture content is determined from tissue compliance data, e.g., measurement of tissue displacement divided by an applied force, or optical clarity. The additional sensor module may include an infrared or optical sensor for sensing (measuring) light or energy generated by a source, such as an infrared or other light source, which is transmitted through or reflected from the tissue, where the sensed value is indicative of tissue moisture content and/or tissue type of tissue proximate a surgical site. An initial tissue moisture content value and/or tissue type may be provided to a control module as a pre-surgical parameter. Sensed real time moisture content values and/or changes in moisture content over time (Δ(difference) moisture content/Δ(difference) time) may further be provided to the control module during the surgical procedure, where the control module modulates the electrical surgical output in accordance with the sensed real time moisture content values and/or changes in moisture content values over time.

As can be appreciated therefore, since electrosurgical devices are energy based by nature, electrosurgical devices, including radiofrequency (RF), ablation, and similar energy based medical devices have sensors to monitor energy delivery. Such sensors include voltage and current measuring devices. Voltage and current measurement are direct indicators of safety parameters of the electrosurgical instrument and are indirect indicators of tissue impedance and correspondingly of tissue hydration. Tissue hydration affects the degree of cooling and heat transfer available through the local water content of the tissue to prevent overdessication.

SUMMARY

The present disclosure advances the state of the art of controlling the energy input from an electrosurgical device by adjusting the hydration level and direction of water motility to significantly increase the likelihood of prevention of overdessication and to initiate tissue division.

More particularly, the present disclosure relates to a method for performing an electrosurgical procedure at a surgical site on a patient. The method includes the step of: continually sensing electrical and physical properties proximate the surgical site. The step of continually sensing properties includes acquiring readings of tissue electrical impedance with respect to time at the surgical site; identifying the minima and maxima of the impedance readings with respect to time; and correlating at least one of the minima and the maxima of the impedance readings with at least one of hydration level and hydraulic conductivity in the tissue at the surgical site. The method also includes controlling the application of electrosurgical energy to the surgical site to vary energy delivery based on the step of correlating at least one of the minima and the maxima of the impedance readings with at least one of the hydration level and the hydraulic conductivity in the tissue at the surgical site.

BRIEF DESCRIPTION OF THE DRAWINGS

Various embodiments will be described herein below with reference to the drawings wherein.

DETAILED DESCRIPTION

Figure 1:
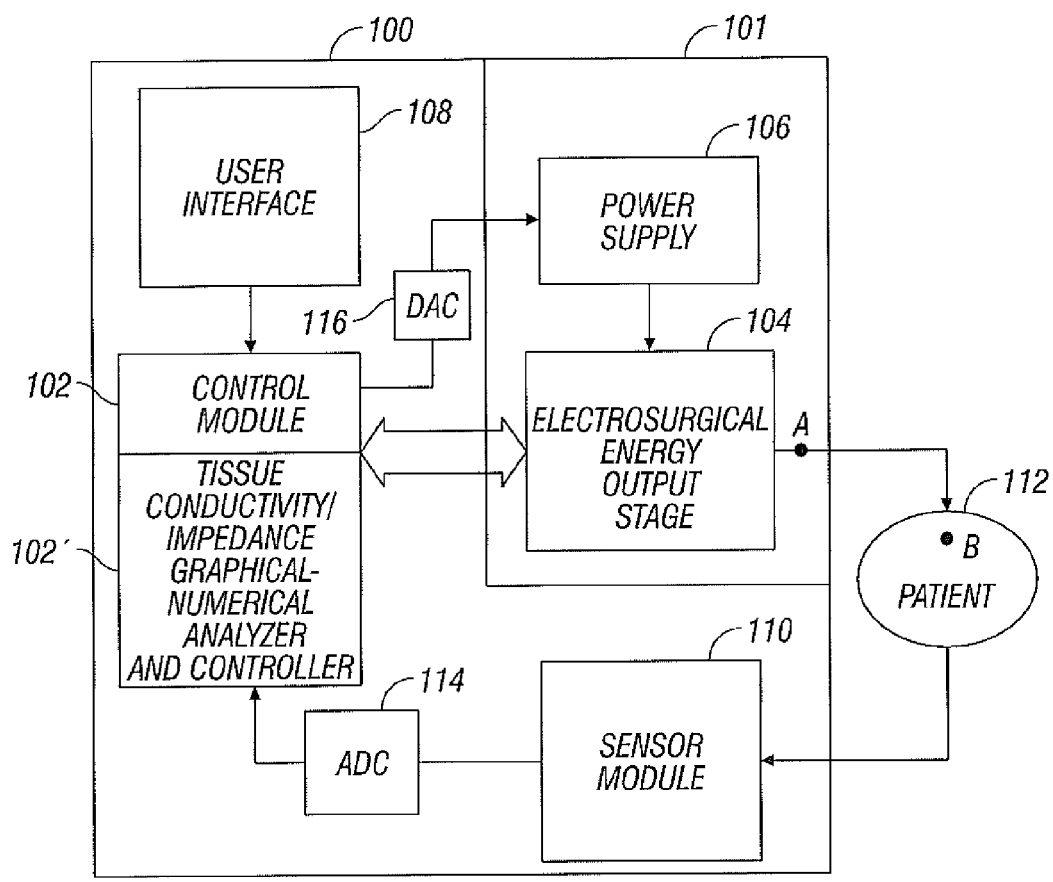
FIG. 1 is a schematic diagram of a closed-loop control system for use with an electrosurgical generator according to the present disclosure.

As described in the background, electrical and thermal conductivity properties of tissue that are exhibited during the application of electrosurgical energy to tissue have been well elucidated in the field.

The present disclosure advances the state of the art of the application of electrosurgical energy to tissue by introducing the concept of hydraulic conductivity (also referred to as water motility) and illustrating how impedance information can be interpreted to measure this parameter.

Hydraulic conductivity, symbolically represented herein as "K", is a property of vascular or capillary beds that, in contrast to the simple measure of moisture content of tissue, describes the ease with which water can move through pore spaces or fractures. "K" depends on the intrinsic permeability of the tissue and on the degree of saturation. One application of hydraulic conductivity "K" is as a factor in the Starling equation, which enables calculation of flow across walls of capillaries and introduces the idea of a reflection coefficient.

The Starling equation is defined as follows:

$$J_v = K_f ([P_c - P_i] - \sigma[\pi_c - \pi_i]) \quad (1)$$

where:

$([P_c - P_i] - \sigma[\pi_c - \pi_i])$ is the net driving force, $K_f$ is the proportionality constant, and $J_v$ is the net fluid movement between compartments.

According to Starling's equation, the movement of fluid depends on six variables:

1. Capillary hydrostatic pressure ($P_c$)
2. Interstitial hydrostatic pressure ($P_i$)
3. Capillary oncotic pressure ($\pi_c$)
4. Interstitial oncotic pressure ($\pi_i$)
5. Filtration coefficient ($K_f$)
6. Reflection coefficient ($\sigma$)

(Oncotic pressure, or colloid osmotic pressure, is a form of osmotic pressure exerted by proteins in blood plasma that usually tends to pull water into the circulatory system).

By convention, outward force is defined as positive, and inward force is defined as negative. The solution to the equation is known as the net filtration or net fluid movement ($J_v$). If positive, fluid will tend to leave the capillary (filtration). If negative, fluid will tend to enter the capillary (absorption). This equation has a number of important physiologic implications, especially when pathologic processes grossly alter one or more of the variables.

More generally, hydraulic conductivity is the proportionality constant in Darcy's law, which relates the amount of water which will flow through a unit cross-sectional area of aquifer under a unit gradient of hydraulic head. It is analogous to the thermal conductivity of materials in heat conduction, or the inverse of resistivity in electrical circuits. The hydraulic conductivity ("K"—the English letter "kay") is specific to the flow of a certain fluid (typically water, sometimes oil or air); intrinsic permeability ("κ"—the Greek letter "kappa") is a parameter of a porous media which is independent of the fluid. This means that, for example, "K" will increase if the water in a porous medium is heated (reducing the viscosity of the water), but "κ" will remain constant. "K" and "κ" are related through the following equation:

$$K = (\kappa \gamma)/\mu \quad (2)$$

where

"K" is the hydraulic conductivity [$LT^{-1}$ or m s$^{-1}$];

"κ" is the intrinsic permeability of the material [$L^2$ or m$^2$];

"γ" is the specific weight of water [$ML^{-2}T^{-2}$ or N m$^{-3}$], and;

"μ" is the dynamic viscosity of water [$ML^{-1}T^{-1}$ or kg m$^{-1}$ s$^{-1}$].

and where

"L"=length or meters (m);

"T"=time or seconds (s); and

"M"=mass or kilograms (kg)

The reflection coefficient relates to the permeability of the tissue. If the permeability of the particular sample of tissue is high as compared to another sample of tissue, the reflection coefficient of the particular sample of tissue is lower than the reflection coefficient of the sample of tissue that is less permeable. This is because more water will pass through the more permeable sample of tissue and less will be reflected back (analogous to the flow of water through a net). Conversely, when the permeability is low, more water will be reflected back and thus the reflection coefficient is comparatively higher (analogous to the flow of water hitting a solid wall rather than a net). Since a solid or a fluid in motion, e.g., a steam pocket, will create an instantaneous dynamic load on a stationary object in its path, the dynamic load on the tissue will be higher when the reflection coefficient of the tissue if higher. As the dynamic load increases, the greater the susceptibility of the particular sample of tissue to tissue division and, when desired, to tissue destruction.

All-in-all, it is easier to explain Darcy's equation using the "hydraulic conductivity" term. It should be mentioned that the Starling Equation (1) accounts for both hydraulic and osmotic pressures that are not specified in the more generalized Darcy Equation (2).

As is known in the art, the water contained within the patient tissue is the solvent that separates and mobilizes the electrically charged ions in the solvent to create an ionic solution. The ionic solution is characterized by the current density or ion flow that creates the desired surgical effect. Without water and the dissolved or solute ions therein, no, or extremely limited electrical current, can be conveyed through the tissue because the tissue would then be characterized by a high electrical impedance. The parameter of hydraulic conductivity "K" provides a metric for how readily water can travel through the tissue when energy is applied. When temperatures cause the tissue water to boil, the gas bubbles that form displace liquid water only at the rate that hydraulic conductivity allows. Water is displaced easily if hydraulic conductivity is high; so water can move away from the boiling site easily and can also rehydrate previously dehydrated tissue very rapidly.

If hydraulic conductivity is low then the pressure of water phase transition may become explosively high. The pressure may create steam jets that find paths of least resistance to areas of lower pressure. These steam jets may create paths along the tissue-device boundary and vent to remote cavities or the atmosphere. If these "steam jets" are created in a controlled manner, then work, such as tissue division, can occur. The application of this tissue division as a function of different states of hydraulic conductivity is discussed below with respect to FIG. 5. As described herein, the tissue division occurs directly or indirectly due to the application of electrical energy, in contrast to tissue division that occurs mechanically, such as via a knife blade in an electrosurgical instrument.

For example, it is desired for liver trans-sections to create bloodless zones to remove a lobe in the liver without blood loss and without a separate cutting step. In conventional ablation processes, although heated and containing coagulated blood, the tissue remains substantially intact. In the embodiments of the present disclosure, the surgeon can cause tissue division by the process of measuring the impedance levels and applying electrosurgical energy to the tissue, effectively cutting the tissue due to the electrical energy of the ablation process itself without requiring a separate step of mechanically cutting the tissue.

Turning the discussion now to the detailed description of the embodiments of the present disclosure, reference should be made to the drawings where like reference numerals refer to similar elements throughout the various figures, Referring to FIG. 1, there is shown a schematic diagram of one embodiment of the presently disclosed closed loop control system 100 for use with an electrosurgical generator 101. Control system 100 includes a control module 102, user interface 108 and sensor module 110. The control module 102 is operatively connected to the electrosurgical generator 101. The electrosurgical generator 101 may include electrosurgical energy output stage 104 and a power supply 106, where the output stage 104 receives power from the power supply 106 and delivers RF energy to a patient 112 via at least one electrode (not shown). As can be appreciated, one or more electrodes may be used with the electrosurgical instrument for performing monopolar or bipolar surgery.

The sensor module 110 senses various electrical and physical parameters or properties at the operating site and communicates with the control module 102 to regulate the electrosurgical output from the output stage 104. The sensor module 110 may be configured to measure or "sense" various electrical or electromechanical conditions at the operating site such as: tissue impedance, changes in tissue impedance, maxima and minima of tissue impedance, tissue temperature, changes in tissue temperature, leakage current, applied voltage and applied current. The sensor module 110 may measure one or more of these conditions continuously or in "real time" such that the control module 102 can continually modulate the electrosurgical output according to a specific purpose or desired surgical intent. More particularly, analog signals provided by the sensor module 110 are converted to digital signals via an analog-to-digital converter (ADC) 114, which in turn are provided to the control module 102.

The control module 102, thereafter, regulates the power supply 106 and/or the output stage 104 according to the information obtained from the sensor module 110. The user interface 108 is electrically connected to the control module 102 to allow the user to control various parameters of the electrosurgical energy output to the patient 114 during surgery to manually set, regulate and/or control one or more electrical parameters of the delivered RF energy, such as voltage, current, power, frequency, amplified, and/or pulse parameters, e.g., pulse width, duty cycle, crest factor, and/or repetition rate depending upon a particular purpose or to change surgical intent.

The control module 102 includes at least one microprocessor capable of executing software instructions for processing data received by the user interface 108 and the sensor module 110 for outputting control signals to the output stage 104 and/or the power supply 106, accordingly. The software instructions executable by the control module are stored in an internal memory in the control module 102, an internal or external memory bank accessible by the control module 102 and/or an external memory, e.g., an external hard drive, floppy diskette, CD-ROM, etc. Control signals from the control module 102 to the electrosurgical generator 101 may be converted to analog signals by a digital-to-analog converter (DAC) 116.

In particular, for the purposes of highlighting the difference between the present disclosure and the prior disclosure of U.S. Patent Application Publication US 2007/0038209 A1, the control module 102 further includes a dedicated tissue conductivity/impedance graphical or numerical hydration analyzer and controller module 102' that performs a graphical and/or numerical analysis of tissue conductivity/impedance data as sensed by the sensor module 110. As explained in more detail below with respect to FIG. 5, the graphical and/or numerical analysis is specifically directed to identifying specific portions of the maxima and minima of the tissue conductivity/impedance data that correlate to hydration level and direction of water motility. Alternatively, the control module 102 is programmed with machine-readable code to perform the aforementioned graphical and/or numerical analysis and control.

The power supply 106 is a high voltage DC power supply for producing electrosurgical current, e.g., radiofrequency (RF) current. Signals received from the control module 102 or hydration analyzer and controller module 102' control the magnitude of the voltage and current output by the DC power supply based on the data readings for maxima and minima of the tissue conductivity/impedance. The output stage 104 receives the output current from the DC power supply and generates one or more pulses via a waveform generator (not shown). As can be appreciated, the pulse parameters, such as pulse width, duty cycle, crest factor and repetition rate are regulated in response to the signals received from the control module 102 based on those portions of the data readings for maxima and minima of the tissue conductivity/impedance that specifically relate to hydration level and direction of water motility. Alternatively, the power supply 106 may be an AC power supply, and the output stage 104 may vary the waveform of the signal received from power supply 106 to achieve a desired waveform.

As mentioned above, the user interface 108 may be local to or remote from the control module 102 or hydration analyzer and controller module 102'. A user may enter data such as the type of electrosurgical instrument being used, the type of electrosurgical procedure to be performed, and/or the tissue type upon which the electrosurgical procedure is being performed. The closed loop control system 100, in particular the sensor module 110, may include, in addition to the sensors that detect voltage and current to determine the maxima and minima of tissue impedance, one or more smart sensors which provide feedback to the surgeon relating to one or more of these physical parameters. Furthermore, the user may enter commands, such as a target effective voltage, current or power level to be maintained, or a target response e.g., change in regulation of the power supply 106 and/or output stage 104, to changes in sensed values, such as an effective change in voltage, current and/or power level as a function particularly of those portions of the data readings for maxima and minima of the tissue conductivity/impedance that specifically relate to hydration level and direction of water motility. The user may also enter commands for controlling electrical parameters of the RF energy, delivered by the electrosurgical generator 101, as described above. Default values may be provided for the above target levels and target responses.

The sensor module 110 includes a plurality of sensors (not shown) strategically located for sensing various properties or conditions at or proximate points "A" and "B". Sensors positioned at or proximate point "A" (hereinafter referred to as at point "A") sense properties and/or parameters of electrosurgical output from output stage 104, and/or properties, parameters or conditions prior to surgical effect of the currently administered electrosurgical energy during the surgical procedure. For example, sensors positioned at point "A" may be provided with or attached proximate the generator 101.

Sensors positioned at or proximate point "B" (hereinafter referred to as at point "B") sense parameters, properties and/or conditions at or across the operating site prior to the surgical procedure and/or in response to surgical effect during the surgical procedure. One or more of these sensors may be included with the electrosurgical instrument, (e.g., on one end effector or opposing end effectors) or attached proximate the operating site. For example, optical sensors, proximity sensors, temperature sensors may be used to detect certain tissue characteristics, and electrical sensors may be employed to sense other parameters of the tissue or operating effects. It is noteworthy that point "A" may be located proximate the surgical site "B" at a location where the signals outputted by the generator 101 are propagated before they are applied or approximately when they are applied to the surgical site "B".

The sensors are provided with leads or wireless means for transmitting information to the control module, where the information is provided directly to the control module 102 and/or to the hydration analyzer and controller module 102', and/or provided to the control module 102 and/or to the hydration analyzer and controller module 102' via the sensor module 110 and/or the ADC 114. The sensor module 110 may include means for receiving information from multiple sensors, and providing the information and the source of the information (e.g., the particular sensor providing the information) to the control module 102 and/or to the hydration analyzer and controller module 102'.

Related prior art methods and systems for controlling the output of electrosurgical generators are described in commonly owned U.S. Patent Application Ser. No. 11,585,506 filed on Oct. 24, 2006 by Buysse et al., now previously mentioned U.S. Patent Application Publication 2007/0038209 A1, entitled "METHOD AND SYSTEM FOR CONTROLLING OUTPUT OF RF MEDICAL GENERATOR", which is a divisional of U.S. patent application Ser. No. 10/427,832 filed on May 1, 2003 and now U.S. Pat. No. 7,137,980 issued on Nov. 21, 2006 to Buysse et al., "METHOD AND SYSTEM FOR CONTROLLING OUTPUT OF RF MEDICAL GENERATOR"; U.S. patent application Ser. No. 10/073,761, filed on Feb. 11, 2002, by Wham et al., now U.S. Patent Application Publication 2003/0004510 A1, entitled "VESSEL SEALING SYSTEM"; and U.S. patent application Ser. No. 09/408,944, now previously mentioned U.S. Pat. No. 6,398,779, filed on Sep. 30, 1999 by Buysse et al., entitled "VESSEL SEALING SYSTEM", which claims the benefit of the priority date for U.S. provisional application No. 60/105,417, filed on Oct. 23, 1998, the entire contents of all of these applications are hereby incorporated by reference herein in their entirety.

Figure 2:
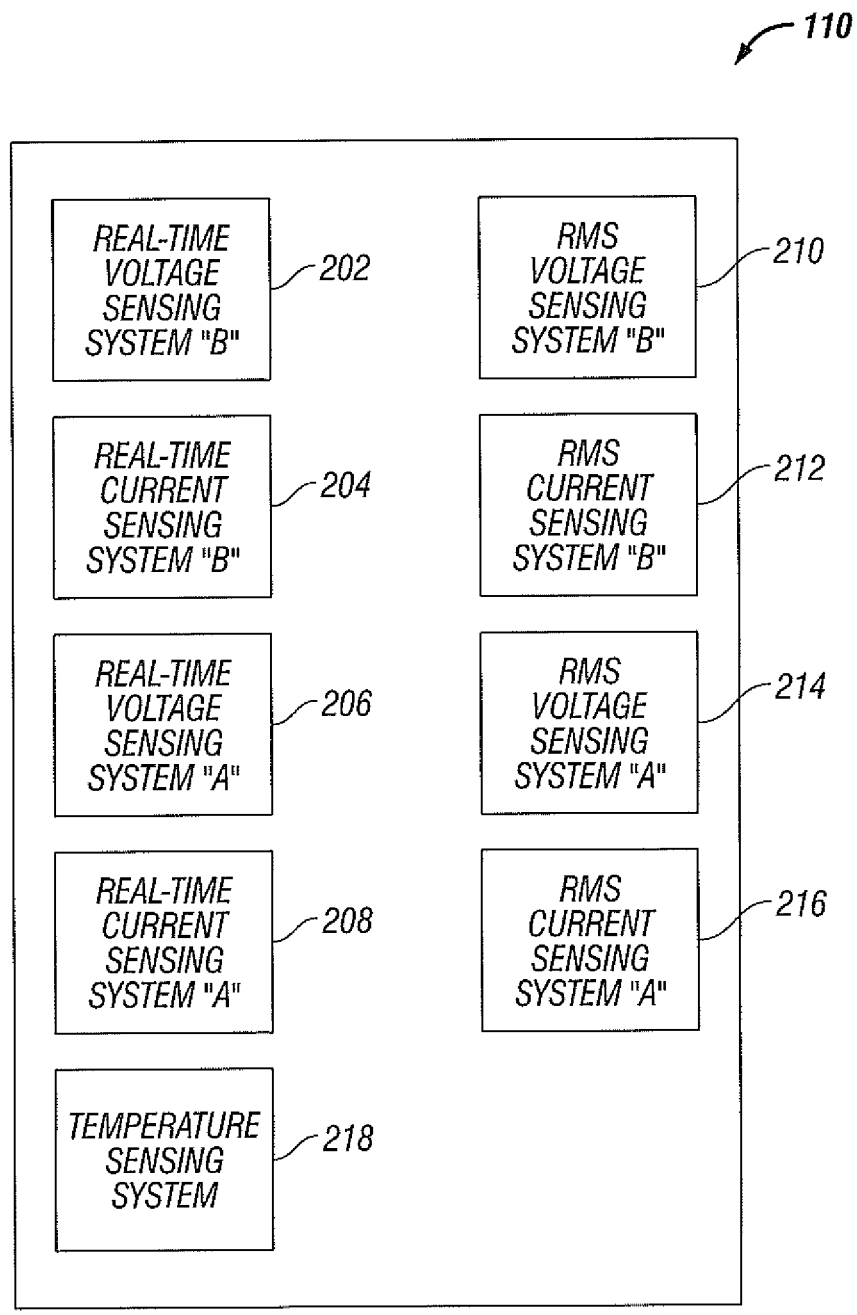
FIG. 2 is a schematic diagram of a sensor module for use with the closed-loop control system of FIG. 1.

With reference to FIG. 2, in addition to FIG. 1, the inner-working components of the sensor module 110 are shown in greater detail. More particularly, the sensor module 110 may include a real-time voltage sensing system 202 and a real-time current sensing system 204 for sensing real-time values for applied voltage and current at the surgical site "B". The sensor module 110 also may include a real-time voltage sensing system 206 and a real-time current sensing system 208 for sensing real-time values of signals returned from the patient at a point "A". An RMS (root-mean-square) voltage sensing system 210 and an RMS current sensing system 212 are also included for sensing and deriving RMS values for applied voltage and current at the surgical site "B", and an RMS voltage sensing system 214 and an RMS current sensing system 216 are included for sensing and deriving RMS values of signals at point "A". A temperature sensing system 218 may be included for sensing tissue temperature at the surgical site "B". Real-time and RMS current and voltage sensing systems are known in the art. The sensor module 110 may further include sensors (not shown) for sensing voltage and current output by the generator 101.

The real time voltage sensing system "A" 206 may be configured as a part of a real time control loop to control the energy output of generator 101 because the sensing and controlling must be done in real time. Regarding the RMS voltage sensing and the RMS voltage sensing system "A" 214, the output of generator 101 is at a high frequency (radiofrequency) which is at a different time base than the impedance change. It is contemplated that impedance change in tissue is thermally induced; and the tissue-thermal interaction of this sort is several orders of magnitude slower than the radiofrequency voltage applied through the generator 101.

The measured or sensed values are further processed, either by circuitry and/or a processor (not shown) in the sensor module 110 and/or by the control module 102 or the hydration analyzer and controller module 102', for deriving changes in sensed values and tissue impedance at the surgical site "B". Tissue impedance and changes in tissue impedance may be determined by measuring the voltage and/or current across the tissue and/or calculating changes thereof over time, and comparing the voltage and current values to known and/or desired values associated with various tissue types for use by the control system 100 to drive electrical output to achieve desired impedance and/or change in impedance values and corresponding maxima and minima of tissue impedance indicative of tissue hydration levels and water motility. As can be appreciated, these known and/or desired values, tissue types and ranges may be stored in an internal look-up table, "a continuous value map" or in an external searchable memory. Commonly owned U.S. Pat. No. 6,398,779 (previously mentioned), U.S. Pat. Nos. 6,203,541, 5,827,271 and U.S. Patent Application Publication No. 2003/0004510 (previously mentioned) disclose methods for measuring tissue impedance, and are incorporated by reference herein in their entirety.

Deriving tissue impedance (or other physical and electrical parameters) from real-time value(s) may provide the benefit of monitoring real-time tissue impedance and/or changes in tissue impedance. As the surgical procedure proceeds, it is believed that the tissue impedance fluctuates in response to removal and restoration of liquids from the tissue at the surgical site "B". As the control module 102 and/or hydration analyzer and controller module 102' monitors the tissue impedance and changes in tissue impedance (or other physical and electrical parameters) the control module 102 and/or hydration analyzer and controller module 102' regulates the power supply 106 and output stage 104 accordingly for achieving the desired and optimal electrosurgical effect based on the specific portions of the impedance/conductivity readings that correlate to hydration level and direction of water motility.

Before beginning an electrosurgical procedure, an operator of the electrosurgical instrument enters information via the user interface 108. Information entered includes, for example, the type of electrosurgical instrument being used, the type of procedure being performed (i.e., desired surgical effect), the type of tissue, relevant patient information, and a control mode setting. The control mode setting determines the amount of or type of control that the control module 102 and/or hydration analyzer and controller module 102' will provide. As mentioned above, one or more sensors (not shown) may also be included to automatically provide information to the control module 102 and/or hydration analyzer and controller module 102' relating to tissue type, initial tissue thickness, initial tissue impedance, etc. Measurement of tissue impedance to detect indications of hydration levels and water motility is discussed in more detail below with respect to FIG. 5.

Exemplary modes include, but are not limited to, one or a combination of one or more of the following modes: a first mode wherein the control module 102 maintains a steady selected output power, current and/or voltage value at site "A"; a second mode wherein the control module 102 and/or hydration analyzer and controller module 102' maintains a steady selected output power, current and/or voltage value at site "B"; a third mode wherein the control module 102 and/or hydration analyzer and controller module 102' maintains a variable selected output power, current and/or voltage values at site "A" which is dependent upon (i.e., a function of) time value(s) and/or sensed parameter(s) or changes in sensed parameter(s) during the procedure; a fourth mode wherein the control module 102 or hydration analyzer and controller module 102' maintains a variable selected output power, current and/or voltage values at site "B", which is dependent upon (i.e., a function of) time value(s) and/or sensed parameter(s) or changes in sensed parameter(s) during the procedure.

According to the embodiments of the present disclosure, another "mode" is detecting the hydraulic conductivity (water motility) and adjusting the rate of energy application that achieves the desired tissue effect. This is accomplished by measuring the intrinsic permeability "$\kappa$", of the material $[L^2$ or $m^2]$ at the particular specific weight "$\gamma$" of the water $[ML^{-2}T^{-2}$ or $N\ m^{-3}]$; and the particular dynamic viscosity "$\mu$" of water $[ML^{-1}T^{-1}$ or $kg\ m^{-1}\ s^{-1}]$ in the tissue being treated. More particularly, the absolute values of the intrinsic permeability, the specific weight, and the dynamic viscosity are not measured, but instead only changes, e.g., an increase or a decrease, in hydraulic conductivity $\Delta K$. are measured.

Another mode according to the embodiments of the present disclosure is tissue division which is performed having the benefit of the knowledge of the hydraulic conductivity. This is discussed further below with respect to FIG. 5. If hydraulic conductivity is low, hydraulic pressure within tissue increases more quickly with any energy deposition. Rapid rises in tissue hydraulic pressure assist in tissue division.

Functions performed on the time value(s) and sensed properties(s) include operations such as calculations and/or look-up operations using a table or map stored by or accessible by the control module 102 and/or hydration analyzer and controller module 102'. The control module 102 and/or hydration analyzer and controller module 102' processes the selected output power, current and voltage values, such as by performing calculations or table look up operations, to determine power control signal values and output control values.

The control module 102 and/or hydration analyzer and controller module 102' may determine initial settings for control signals to the power supply 106 and the output stage 104 by using and/or processing operator-entered data or settings, performing calculations and/or accessing a look-up table stored by or accessible by the control module 102 and/or hydration analyzer and controller module 102'. Once the electrosurgical procedure begins, the sensors of sensor module 110 sense various physical and electrical properties and provide feedback to the control module 102 and/or hydration analyzer and controller module 102' through the ADC 114 as needed. The control module 102 and/or hydration analyzer and controller module 102' processes the feedback information in accordance with the pre selected mode, as well as any additional operator-entered commands entered during the procedure. The control module 102 and/or hydration analyzer and controller module 102' then sends control information to the power supply 106 and the output stage 104. The generator 101 may be provided with override controls, to allow the operator to override the control signals provided by the control module 102 and/or hydration analyzer and controller module 102', if needed, e.g., by entering override commands via the user interface 108.

Figure 3:
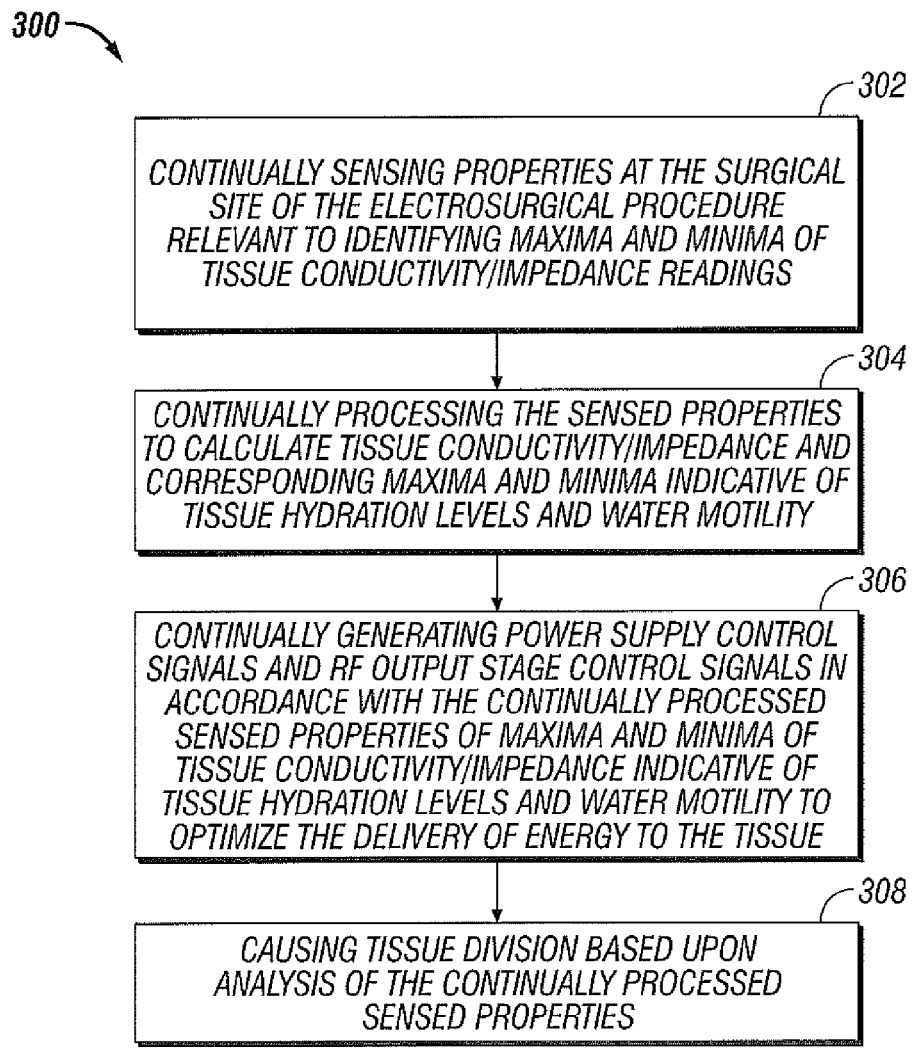
FIG. 3 is a flowchart illustrating a method of operation of the closed-loop control system according to the present disclosure.

FIG. 3 shows a flow chart illustrating a method 300 for controlling operation of the closed loop control system 100 during an electrosurgical procedure in accordance with an embodiment of the present disclosure. At step 302, the method includes continually sensing various physical and electrical properties at the surgical site that are relevant to identifying those portions of the maxima and minima of tissue conductivity/impedance readings that are specifically correlated with tissue hydration level and direction of water motility. At step 304, the sensed properties are continually processed to calculate tissue conductivity/impedance and corresponding minima and maxima indicative of tissue hydration levels and water motility. At step 306, power supply control signals are continually generated for controlling the magnitude of the signals output by the electrosurgical generator and output stage control signals are continually generated, for controlling pulse parameters of the output signals in accordance with the continually-processed sensed properties of maxima and minima of tissue conductivity/impedance that are indicative of tissue hydration levels and water motility, thereby controlling the flow of water through the tissue to optimize the delivery of energy to the tissue and thus enhancing the therapeutic effect of the particular energy treatment being applied. At step 308, the method includes causing tissue division based upon analysis of the continually processed sensed properties.

The sensor module 110 may further include a proximity sensor for sensing (measuring) tissue thickness proximate the surgical site "B", and generating a tissue thickness value. An initial tissue thickness value may be provided to the control module 102 as a pre-surgical parameter. Sensed real time tissue thickness values and/or changes in tissue thickness values over time (Δ[difference] thickness/Δ[difference] time) may further be provided to the control module 102 and/or hydration analyzer and controller module 102' during the surgical procedure, where the control module 102 and/or hydration analyzer and controller module 102' modulates the electrical surgical output in accordance with the sensed real time tissue thickness values and/or changes in tissue thickness values over time as the tissue thickness values and/or changes in thickness are related to the hydration levels and water motility in the tissue that are determined by analyzing those portions of the maxima and minima of the impedance/conductivity readings that correlate to the same.

Accordingly, the present disclosure provides a closed loop control system 100 for providing continual control of the power supply 106 and the output stage 104 in response to "sensed" physical or electrical properties at the surgical site and/or proximate the output stage.

Figure 4:
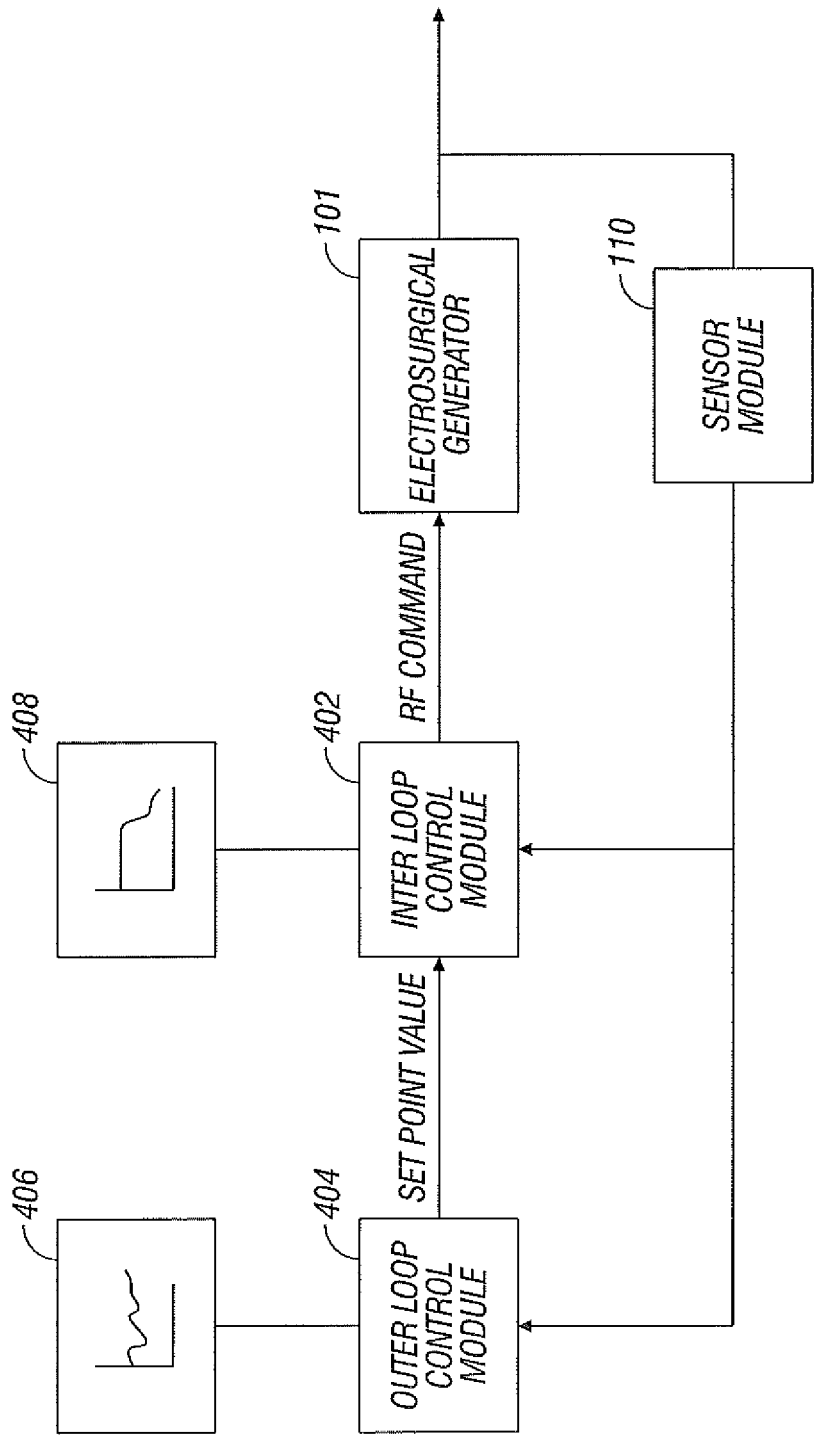
FIG. 4 is a block diagram of a dual loop control system in accordance with another embodiment of the present disclosure.

In an additional embodiment according to the present disclosure and in particular reference to FIG. 4, the control module 102 and/or hydration analyzer and controller 102' is provided with two control loops, an inner loop controlled by inner loop control module 402 and an outer loop controlled by outer loop control module 404. The inner and outer loop control modules 402, 404 are software modules executable by a processor of the control module 102 and/or hydration analyzer and controller 102'. The inner and outer loop control modules 402, 404 both receive signals generated by sensor module 110.

The inner loop control module 402 controls the amount of current, voltage and/or power delivered to the tissue for controlling a variable, e.g., I, V or P, sensed at the tissue and/or calculated from sensed values, until a desired event occurs (a rapid dz/dt or impedance rise is achieved), e.g., an impedance value is reached that is in one embodiment in the range of about 50 ohms to about 400 ohms. The control variable is controlled to change during the course of the seal cycle according to impedance value (or other sensed and/or derived values), as determined by generator limitations (power, current, voltage) and surgical limitations (maximum limits for application of energy to tissue).

The inner loop control module 402 continually receives real time sensed values, such as current I and voltage V, from the sensor module 110 and may perform calculations on the received values for deriving additional real time values, such as power P and impedance Z. A desired inner loop value for I, V, and/or P are obtained by accessing at least one stored inner mapping of continuous values 408, look-up table or equivalent, where the inner mapping 408 may be in accordance with a function of impedance. In one embodiment, the inner loop control module 402 consults the inner mapping 408 for obtaining the desired inner loop value for the impedance currently being sensed and derived.

An algorithm is used to compare the real time value of I, V and/or P to the respective desired inner loop value and output an RF command to the electrosurgical generator 101 accordingly for achieving the desired inner loop value without exceeding the desired inner loop value, e.g., the RF command raises the target current, voltage and/or power output by the electrosurgical generator 101 when the real time value for I, V and/or P is lower than the respective desired inner loop value for I, V and/or P, and vice versa. It is contemplated that the RF command controls waveform parameters of electrosurgical energy output by the electrosurgical generator 101, including current, power, voltage, duty cycle, frequency, waveshape, etc. It is further contemplated that the inner loop is used without the outer loop for achieving the desired tissue effect.

The outer loop control module 404, layered over the inner loop control module 402, provides additional control of a variable for reaching a desired output value or effect. For example, control of the variable may monitor/regulate the rate of change of impedance of the tissue (sensed and calculated). In different embodiments, the variables controlled may include temperature, rate of change of temperature, and/or the energy input to the tissue. Outer loop control module 404 continually receives sensed values, such as I, V and temperature T from the sensor module 110 at a time "t" and performs calculations on the sensed values and in one embodiment stored values for deriving values such as rate of change of impedance and/or rate of change in temperature. For example, the value for change in impedance (dz/dt) is obtained in accordance with:

$$dz/dt=(Z-Z\_OLD)/(t-t\_OLD); \qquad (3)$$

$$Z\_OLD=Z;$$

where Z is the impedance in accordance with values measured at time t; and Z_OLD is the stored impedance in accordance with values measured at a previous time interval at time t_OLD An outer loop desired value for the control variable is obtained by accessing a stored outer mapping of continuous values 406, or alternatively a table or equivalent. The desired rate of change according to outer mapping 406 may be steady, or may depend on the stage of the seal cycle and change over time. The tissue is in a dynamic state during the seal procedure, and the outer loop monitors the rate of change throughout the procedure to determine the degree to which the desired rate of change is being achieved. When the control variable is temperature, a temperature map may be used for outer mapping 406 in which desired temperature is plotted versus time. When the control variable is rate of change in temperature, a rate of change in temperature map may be used for outer mapping 406 in which desired temperature is plotted versus time. Energy may be applied in a similar fashion, where an energy function can be calculated using equations derived for specific tissue types or using sensed values.

An algorithm is used to compare the real time sensed/calculated value of rate of change of impedance, temperature, rate of change of temperature and/or energy at time "t" to the respective desired outer value at time "t" obtained from the outer mapping 406 for determining if the desired outer value is met, and if not, for determining the ratio of the difference between the real time value and the desired outer value to the desired outer value. If the desired outer value is not being met, the outer loop module 406 generates a set point value which is provided to the inner loop module 402. The set point value is raised when the real time value for rate of change of impedance, temperature and/or rate of change of temperature is lower than the respective desired outer value for rate of change of impedance, temperature and/or rate of change of temperature, and vice versa.

The set point value may be a ratio signal for altering the inner mapping 408 by raising or lowering a plotted curve of the inner mapping 408 along the y-axis. The ratio signal may be a proportional integral derivative (PID) control signal, as is known in the art. The inner loop control module 402 responds instantaneously by accessing the altered inner mapping 408 for obtaining a desired inner value from the outer loop, comparing the real time value of the control variable, generating an RF command for achieving the desired inner value without exceeding the desired inner value, and outputting the RF command accordingly to the electrosurgical generator 101 for controlling voltage, current and/or power needed for achieving a desired tissue effect.

In one embodiment, the outer loop control module 404 uses the real time value of rate of change of impedance, temperature, rate of change of temperature, and/or total energy delivered to determine if a desired outer value has been reached which indicates completion of a seal. Upon determination of seal completion, a stop signal is generated for stopping the sealing process. Otherwise, the outer loop continues to monitor, receive and process sensed values from the sensor module 110.

Control of I, V and/or P by the inner loop control module 402 improves system stability and control capabilities in low impedance ranges, e.g., 0-20 ohms, which are critical for seal initiation, particularly by avoiding a low-end impedance break point which induces oscillation and lack of system control. The outer loop control enhances the control module's ability to control sealing in accordance with desired trends or events, to change seal intensity by changing the rate of change of impedance, and to enhance uniform sealing of tissue, i.e., normalize tissue in terms of variability, including tissue hydration, volume and composition. With feedback control and continuous sensing of the tissue's condition, there is not a need to switch control variables (i.e., low/high end break points), which improves system stability as explained above.

The control module 102 controls a module for producing resistive heat for regulating heat applied to the tissue for achieving the desired tissue effect instead of or in addition to controlling the electrosurgical output stage 104 and/or the power supply 106. The control module 102 responds to sensed tissue temperature or other sensed properties indicative of tissue temperature, accesses at least one mapping, data table or equivalent using the sensed values for obtaining desired output current or resistivity values, and outputs a command signal for controlling output heat resistivity. The module for producing resistive heat may include a current source and/or a variable resistor which are responsive to the command signal for outputting a desired current or providing a desired resistance, respectively.

In another embodiment of the present disclosure, the control system includes a sensor module for sensing at least one property associated with a surgical site during at least one of a pre-surgical time prior to a surgical procedure, the surgical procedure and a post-surgical time following the surgical procedure for generating at least one signal relating thereto; and a control module executable on a processor for receiving said at least one signal and processing each of said signals using at least one of a computer algorithm and a mapping and generating at least one control signal in accordance with the processing, and providing the at least one control signal to the electrosurgical generator for controlling the generator. In one embodiment, the processing includes determining tissue type of tissue proximate the surgical site.

In an additional embodiment, the sensor module 110 (or an additional sensor module (not shown)) senses at least one property as a pre-surgical condition, as a concurrent surgical condition and/or as a post-surgical condition. In one embodiment, the sensor module 110 senses at least two surgical conditions (or changes in surgical conditions over time) selected from pre-surgical, concurrent surgical and post-surgical conditions. Pre-surgical conditions include: degree of opaqueness of tissue proximate the surgical site; moisture content level of the tissue; and/or thickness of the tissue. Concurrent conditions include: degree of opaqueness of the tissue proximate the surgical site; moisture content level of the tissue; thickness of the tissue; temperature of the tissue; impedance of the tissue; current across the tissue; voltage across the tissue; power across the tissue; changes in degree of opaqueness of the tissue; changes in moisture content level of the tissue; changes in thickness of the tissue; changes in temperature of the tissue; changes in impedance of the tissue; location of maxima and minima of impedance readings and specific portions of the maxima and minima that correlate to the hydration level at a specific location in the tissue at or near the electrode-tissue interface and direction of water motility; changes in current across the tissue; changes in voltage across the tissue; and changes in power across the tissue. The post-surgical conditions include: degree of opaqueness of tissue proximate the surgical site; moisture content level of the tissue; thickness of the tissue; temperature of the tissue; and impedance of the tissue.

Electrical cutting (rather than mechanical cutting (i.e., a knife moving through tissue)), referred to below as E-cutting of tissue, is facilitated depending on whether the tissue is permeable or not permeable. External pressure is applied on the tissue by the jaws of the electrosurgical instrument while internal pressure, alternatively referred to previously as hydraulic pressure, is generated within the tissue by water that expands as its temperature increases above ambient temperature (and its density correspondingly decreases). When the water temperature in the tissue increases above the corresponding boiling point either at atmospheric pressure or under the external pressure applied by the jaws, the water changes phase by transitioning from the liquid phase to the gaseous phase, i.e., the water changes from liquid to steam. The expansion of the water when heated to steam reduces the density of the water but increases the internal pressure in the tissue. The impedance of the tissue increases when steam is formed since the ions are no longer present in the steam to form a conductive medium to enable the electrical current between the electrode surfaces. Since the formation of steam pockets or bubbles within the tissue increases the hydraulic pressure within the tissue, the increase in hydraulic pressure facilitates tissue division particularly when the tissue exhibits a high reflection coefficient, as explained above.

It should be noted that the expansion of the liquid water into steam may occur even after the energy being applied by the electrosurgical generator has been intermittently terminated due to the residual heat of the surrounding tissue and of the electrode or electrodes. Thus the impedance of the tissue can increase even when energy is no longer being applied. In addition, during the intermittent period, water is displaced within the tissue. Tracking of this displacement of water provides information that enhances the accuracy and effectiveness of the process of tissue division being implemented by the electrosurgical system.

As the proteins within the tissue are heated, they become depolymerized and the osmotic pressure is reduced. Such heating of the proteins changes their hydrophilic properties.

Conversely, when energy is no longer being applied for a sufficient period of time, and heat is being transferred to the surroundings, the steam pockets cannot be sustained and instead collapse, resulting in a decrease in the tissue impedance.

By sensing more precisely where in the tissue and when such expansion to steam occurs, the e-cutting process of tissue division can be enhanced and facilitated. In addition, when tissue destruction is the desired result, sensing more precisely where in the tissue and when such expansion to steam occurs also enhances and facilitates tissue destruction.

Figure 5:
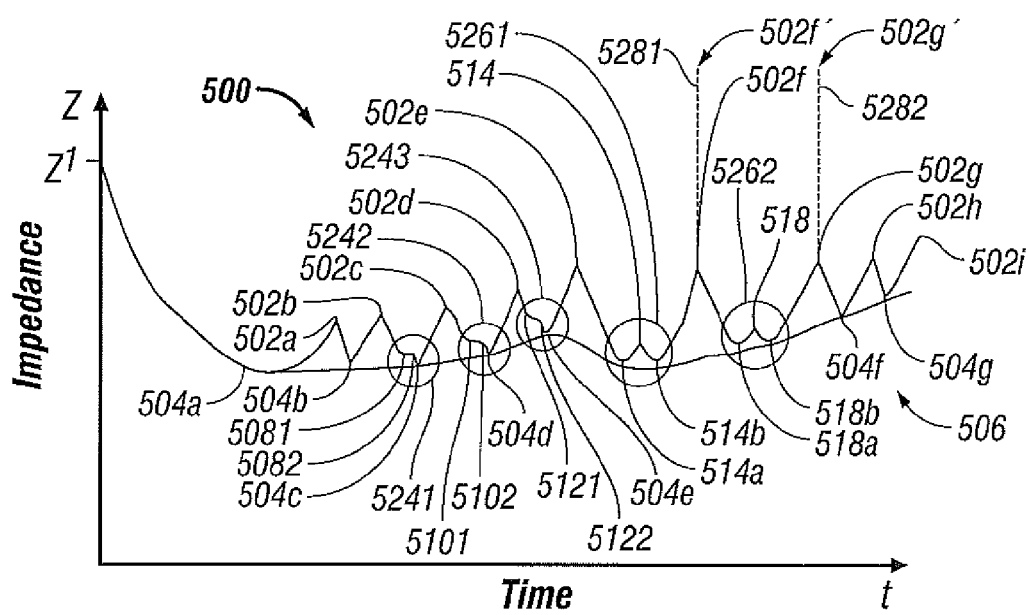
FIG. 5 is a graphical plot of impedance versus time resulting from a tissue ablation process and highlighting times of occurrence of low motility of water in the tissue and of high motility of water in the tissue according to one embodiment of the present disclosure.

The foregoing principles of the present disclosure are illustrated by reference to FIG. 5. More particularly, FIG. 5 illustrates examples of pulsed energy application of impedance versus time as shown by the impedance at relatively lower value then quickly rising to a peak only to fall back to the lower value. This is one energy cycle. During the "off" cycle, a small amount of voltage remains "on" to ensure that the sensors maintain accuracy. (Sensors lose their ability to sense if applied voltage decays to zero). During this "off" time (example: 504b and 502b) tissue is rehydrating and the shape of the impedance curve during the "off" period indicates how permeable the tissue is to water rehydration. The shape of the impedance-time trace indicates if hysteresis occurs during the traverse of the temperature-tissue conductivity curve. Hysteresis of this nature indicates that water is not rehydrating this tissue quickly due to low hydraulic conductivity.

Turning now specifically to FIG. 5, there is disclosed a hypothetical curve 500 for an ablation process of tissue impedance plotted against time that is analyzed in specific detail for precise location of times of occurrence of areas in the tissue of low hydraulic conductivity (water motility) and of high hydraulic conductivity (water motility). It is assumed that the active region of the electrode remains substantially stationary during the ablation process, as in a bi-polar electrode ablation process. As discussed above, the present disclosure relates to a method of measuring voltage and current parameters of an electrosurgical instrument to calculate tissue impedance. If the values of voltage and current are known through measurement, then the impedance of the system can be calculated.

The impedance of all the non-tissue components of the system is generally constant so any fluctuations of the impedance are usually associated with the dynamic changes of the treated tissue. Hence the impedance changes hold valuable information about the dynamic change of tissue properties. One direct application of knowledge of the hydraulic conductivity (water motility) is recognition of when the tissue held between the jaws of an electrosurgical instrument is ready for an energy burst that causes successful tissue division, resulting in an "E-cut," i.e., electrical cutting (rather than mechanical cutting (i.e., knife moving through tissue)), as mentioned above.

As is evident from FIG. 5, the impedance values often change dramatically over the duration of energy based treatments. If the impedance is recorded over time, relative changes can be tracked. For instance, the impedance values often rise and fall rapidly so if the lowest values of impedance are tracked during this process, the tissue hydration can be detected. Also the response of the impedance change to power on or power off conditions can indicate how permeable the tissue is to bulk water movement or the motility of water through the tissue. Hydration levels, further supplemented by the hydraulic conductivity (the motility of water) through the tissue are good indicators of the effectiveness of the energy based treatment because the water is necessary for ionic conduction. As the tissue desiccates during energy treatment, the impedance rises and the application of energy becomes less efficient. Motility of the water is an indicator of the ability of partially desiccated tissue to become re-hydrated.

FIG. 5 illustrates characteristic impedance traces acquired during an operation of an electrosurgical instrument, e.g., a pencil electrode during an ablation procedure. An advancement of the state of the art provided by the present disclosure is the introduction of the premise that rather than being considered system "noise" or system error, as is the collective assessment of those skilled in the art heretofore, there is useful information in the "W-shaped" portion during the "power off" duty cycle of the impedance trace that is indicative of the levels of hydration in the tissue. (See for example FIG. 8 of U.S. Pat. No. 6,575,969 B1).

The impedance trace in FIG. 5 is the total spatial integration of the tissue in contact with the electrode for an ablation process in which the active region of the electrode probe is maintained substantially stationary with respect to the tissue, such as a bi-polar electrode system. Hence directivity of water displacement is not known but the assumption that displacement is in a radial direction away from the high energy field of the active region of the electrode is a reasonable assumption.

In applications of the principles of the present disclosure to vessel sealing, more than one electrode (multiple electrode segments in a jaw), or other sensors, e.g., optical sensors, are required to determine the directivity of water displacement. For example, commonly owned U.S. Patent Application Publication US 2006/0064086 A1 "BIPOLAR FORCEPS WITH MULTIPLE ELECTRODE ARRAY END EFFECTOR ASSEMBLY" by Odom et al. discloses arrays of multiple electrode segments that are each independently powered in each jaw member.

In the ablation process of FIG. 5, it is assumed that the bi-polar electrode probe remains substantially stationary with respect to the tissue so that the measure of impedance in the tissue is generally only a function of time and not of location in the tissue. Specifically, the needle probe (the primary electrode) is positioned substantially stationary with respect to the tissue while the secondary electrode is located remotely from the needle probe. The bi-polar electrode probe directs electromagnetic energy to the tissue and such energy passes through the tissue in the vicinity of the probe and alternates in direction in the tissue as it circuitously travels through the tissue from one active electrode to the other active electrode in the probe. Such electromagnetic energy includes, but is not limited to, radiofrequency waves and microwave radiation. It is assumed that measurable heating of the tissue is limited to a volume of tissue in the vicinity of the active region of the electrode probe and that the remaining tissue distal to the probe remains at body temperature.

[Although the example impedance versus time curve illustrated in FIG. 5 applies to a bi-polar ablation electrode system, application of the principles of the current disclosure to a monopolar ablation electrode system would require that the impedance be measured both with respect to location as well as time. FIG. 8 of commonly owned U.S. Pat. No. 6,575,969 B1 illustrates that, during a mono-polar ablation procedure, a thermosurgery probe 802 is inserted into the patient's body such that the tip of the probe 803 is placed within the target volume 801. The radiofrequency, laser, high frequency, or other power-generating element is represented by component mark number 804. In the case of a high frequency generator, a return element to a reference electrode 805 is attached to the patient's body around the shoulder region. This reference electrode might be a gel-pad, large area, conductive pad or other type of standard reference electrode that is used for a high frequency generator.]

Thus, one embodiment of the present disclosure relates to a method of detecting the hydration and motility of water around an energy applying medical device such as an electrosurgical instrument. Sensing, monitoring and controlling hydration around the energy device ensures that the energy device is ultimately controlled so that energy is delivered to the tissue in the most efficient manner and that the duration of the procedure is the minimum time necessary to achieve the desired tissue effect.

In FIG. 5, precise location of times of occurrence of areas in the tissue of low water motility and of high water motility can be determined from the plot 500 of impedance "Z", that may be measured in ohms, versus time "t". The plot 500 begins with an initial impedance "$Z_1$" and includes a plurality of intermittent crests or peaks 502a, 502b, 502c, 502d, 502e, 502f, 502g, and 502h, i.e., the intermittent maxima, and a corresponding plurality of intermittent troughs or valleys 504a, 504b, 504c, 504d, 504e, 504f and 504g, i.e., the intermittent minima. A curve 506 is drawn that envelopes the minima 504a through 504g.

Following the initial impedance "$Z_1$", which occurs at body temperature, even though energy is applied from the electrosurgical generator 101 such that the local temperature of the tissue rises to about 80 degrees Celsius (° C.), the tissue impedance Z drops to a first minimum at 504a, During the next phase, from minimum 504a to first maximum 502a, energy from the electrosurgical generator 101 is terminated at first maximum or peak 502a. During the approach to peak 502a, the temperature of the water within the tissue has increased to the boiling point, e.g., 100° C., such that a phase change from liquid to vapor occurs, i.e., a steam pocket or bubble has formed within the tissue at peak 502a. As the temperature increases towards the boiling point, the energy continues to be applied and the impedance increases. The phase change to the vapor state causes an increase in hydraulic conductivity. During the decrease in impedance Z from first peak 502a to second minimum 504b, energy remains terminated or turned off, the steam bubble collapses. Osmotic pressure draws water in to fill the void caused by the collapse of the steam bubble. Thus, the increase in water content causes the hydraulic conductivity to increase and the impedance to decrease. Energy is re-applied at second minimum 504b so that the hydraulic conductivity decreases and the impedance increases until second maximum or peak 502b. Again, the temperature of the water within the tissue has increased to the boiling point such that a phase change occurs at second maximum or peak 502b.

Upon reaching the second maximum or peak 502b, energy is again terminated and the tissue re-hydrates until a first curvature change point 5081 occurs wherein a marked change in slope of the impedance curve Z versus t occurs such that the decay in impedance decreases and both the hydraulic conductivity and the impedance remain relatively constant. The energy remains terminated until the impedance Z begins to decrease again, and conversely the hydraulic conductivity begins to increase again, at a second curvature change point 5082 at which time the energy is re-applied, the impedance Z decreases for a short time until a third minimum 504c is reached.

During the decrease in impedance from second maximum 502b to third minimum 504c, the formation of first and second curvature change points 5081 and 5082, respectively, is an indication that tissue hysteresis has occurred. That is, the tissue has "remembered" the prior application of energy and a change in tissue properties has occurred. The change in tissue properties results in reduced hydraulic conductivity during the transition from second maximum 502b to third minimum 504c as compared to the transition from first maximum 502a to second minimum 504b, as indicated by the first and second curvature change points 5081 and 5082, respectively. The motility of the water within the tissue tends to decrease, i.e., the flow of water is inhibited within the tissue.

As application of the energy continues and the tissue dehydrates, the impedance Z increases again sharply until a third maximum or peak 502c is reached. In a similar manner as during the approach to maximum or peak 502b, during the approach to maximum or peak 502c, the temperature of the water within the tissue has increased to the boiling point such that a phase change occurs at third maximum or peak 502c.

Energy is again terminated at third peak 502c. Thereby a first modified V-shape 5241 is formed in the data plot 500 that is indicative of a region in the tissue wherein there is low motility of water.

The rate of tissue rehydration changes after third peak 502c as compared to after second peak 502b. More particularly, the steam bubble or pocket that was formed during the ascent to third peak 502c again collapses and the osmotic pressure causes the water to re-enter the tissue undergoing the ablation process. The rate of increase of hydraulic conductivity decreases until a change in the rate of decrease of impedance Z again occurs at first curvature change point 5101. As compared to the relatively constant impedance Z versus time t occurring after first curvature change point 5081, after first curvature change point 5101, the motility and the hydraulic conductivity of the water in the tissue increase slightly such that the impedance Z decreases slightly until reaching second curvature change point 5102, at which point energy is re-applied until the impedance Z decreases to fourth minimum 504d. Again, the formation of first and second curvature change points 5101 and 5102, respectively, is indicative of tissue hysteresis and thus a change in the properties of the tissue due to the ablation process.

Again, as application of the energy continues and the tissue dehydrates, the impedance Z increases again sharply until a fourth maximum or peak 502d is reached. Energy is again terminated at fourth peak 502d. Thereby a second modified V-shape 5242 is formed in the data plot 500 that is also indicative of a region in the tissue wherein there is low motility of water.

The rate of tissue rehydration changes again after fourth peak 502d as compared to after third peak 502c. More particularly, the rate of increase of hydraulic conductivity decreases until a change in the rate of decrease of impedance Z again occurs at first curvature change point 5121. As compared to the impedance Z versus time t occurring after first curvature change point 5101, after first curvature change point 5121, the motility and the hydraulic conductivity of the water in the tissue increase at a more pronounced rate such that the impedance Z decreases at a more pronounced rate until reaching second curvature change point 5122, at which point energy is re-applied until the impedance Z decreases to fifth minimum 504e.

The application of energy continues, the tissue again dehydrates, and the impedance Z increases again sharply until a fifth maximum or peak 502e is reached. Energy is again terminated at fifth peak 502e. Thereby a third modified V-shape 5243 is formed in the data plot 500 that is again indicative of a region in the tissue wherein there is low motility of water.

In contrast to the second modified V-shape 5242, the third modified V-shape 5243 indicates a higher level of hydraulic conductivity since the impedance Z decreases at a faster rate prior to fifth minimum 504e as compared to the second modified V-shape 5242 prior to fourth minimum 504d.

In the example illustrated in FIG. 5, following the termination of the energy at fifth maximum 502e, again the tissue impedance decreases but instead of reaching a sharp minimum such as 504b, 504c, 504d and 504e, a first blunt minimum 514a is formed and the tissue impedance subsequently increases while the energy continues to be terminated until a low impedance maximum 514 is formed, During the time period between the first blunt minimum 514a and the low impedance maximum 514, the tissue becomes less permeable and the amount of water entering the tissue decreases. Correspondingly, the hydraulic conductivity of the tissue decreases. The reduced permeability increases the water reflection coefficient of the tissue.

At low impedance maximum 514, the energy is again applied and the impedance decreases for a brief period until a second blunt minimum 514b is formed. As the application of energy is continued, the impedance increases, while conversely, the hydraulic conductivity decreases, to sixth maximum or peak 502f. The indication of virtual equality of the impedance levels Z at first blunt minimum 514a and second blunt minimum 514b is evidence that the displacement of water within the tissue is substantially equal in both directions. In addition, when the blunt minima in a W-shape are substantially equal, the hydration level and the tissue permeability are equal. The low impedance peak 514 between the two blunt minima 514a and 514b forms a W-shape 5261 that is indicative of a time period during which there is high motility of water in the tissue as compared to the time periods of the modified V-shapes 5241, 5242 and 5243. At the time of occurrence of the blunt minima 514a and 514b, the tissue membranes have a porosity and a reflectance coefficient that are optimal for the occurrence of tissue division upon further application of electrical energy from the electrosurgical generator. The virtual equality of the blunt minima 514a and 514b is indicative of a lack of tissue hysteresis during this time period and as a result no change in tissue impedance. Thus the occurrence of the blunt minima 514a and 514b presents in effect almost a "last opportunity" to effect tissue division using the electrical energy from the electrosurgical generator.

From the initial impedance Z1 to the impedance at sixth maximum 502f, the plot 500 of impedance Z versus time t has followed an electrosurgical ablation procedure according to the prior art in which tissue division was not intended to occur. In the prior art ablation procedure, the significance of the modified V-shapes 5241, 5242 and 5243 and of the W-shape 5261 with respect to tissue hydration and dehydration are disregarded with respect to the control of energy received from the electrosurgical generator 101.

According to the present disclosure, the detailed analysis of the significance of the modified V-shapes 5241, 5242 and 5243 and of the W-shape 5261 with respect to tissue hydration and dehydration are incorporated into a method of initiating tissue division using electrical energy during an ablation process, as opposed to a separate step being required following the ablation process of mechanical cutting of the tissue. More particularly, following the occurrence of the second blunt minimum 514b, the energy from the electrosurgical generator 101 is increased such that the impedance Z increases along the dashed line 5281 to a level at maximum 502f that is greater than the impedance of the tissue at sixth maximum 502f so as to be sufficient to cause tissue division.

In lieu of increasing the energy from the electrosurgical generator 101 upon achieving sixth maximum 502f, in order to verify that a time period of relatively high tissue hydration has occurred, the surgeon may instead choose to continue along the curve 500 by terminating the energy at sixth maximum 502f to allow the tissue impedance Z to decrease to approach a first blunt minimum 518a followed by a low impedance peak 518 at which the energy is again applied and the impedance decreases for a brief period until a second blunt minimum 518b is formed. Again, as the application of energy is continued, the impedance increases, while conversely, the hydraulic conductivity decreases, to seventh maximum or peak 502g. The low impedance peak 518 between the two blunt minima 518a and 518b forms a second W-shape 5262 that is also indicative of a time period during which there is high motility of water in the tissue as compared to the time periods of the modified V-shapes 5241, 5242 and 5243. However, the difference in the level of impedance Z between first blunt minimum 518a and second blunt minimum 518b, i.e., the impedance Z at second blunt minimum 518b is significantly greater than the impedance Z at first blunt minimum 518a, and thus is indicative of the occurrence of tissue hysteresis and a change in properties of the tissue, in contrast to the lack of tissue hysteresis and change in tissue properties associated with blunt minima 514a and 514b.

In the electrosurgical ablation method of the prior art, the energy is again terminated at seventh maximum 502g and the impedance Z decreases to a sharp minimum 504f. Energy is again applied and the impedance increases to eighth maximum 502h. Upon reaching the eighth maximum 502h, energy is again terminated and the impedance Z decreases to a sharp minimum 504g. A final application of energy following minimum 504g results in an increase in impedance to ninth maximum 502i at which point the ablation procedure is terminated without causing tissue division.

In contrast, in the electrosurgical ablation method according to the present disclosure, in lieu of terminating the energy at seventh maximum 502g, having confirmed the presence of the first W-shape 5261, the surgeon may manually, or the software controlling the electrosurgical generator 101 is programmed such that, following the occurrence of the second blunt minimum 518b, the energy from the electrosurgical generator 101 is increased such that the impedance Z increases along the dashed line 5282 to a level at maximum 502g' that is greater than the impedance of the tissue at seventh maximum 502g so as to be sufficient to cause tissue division.

During the transition from blunt minimum 514a to low impedance peak 514, and from blunt minimum 518a to low impedance peak 518, the energy applied forms a steam pocket that causes an increase in impedance. The impedance decreases from low impedance peak 514 to blunt minimum 514b and from low impedance peak 518 to blunt minimum 518b after the energy is terminated following the occurrence of the low impedance peaks 514 and 518.

As the tissue begins to desiccate in the region following the first W-shape 526₁, the magnitude of the difference between the second low impedance peak 518 and the corresponding first blunt minimum 518a as compared to the difference between the second low impedance peak 518 and corresponding second blunt minimum 518b begins to decrease as compared to the magnitude of the difference between the first low impedance peak 514 and the corresponding substantially equal blunt minima 514a and 514b. It can be seen also from the general trend of the enveloping curve 506 that the impedance Z also begins to increase following the first W-shaped region 526₁ since the quantity of water present in the tissue is no longer sufficient to facilitate hydraulic conductivity.

Referring also to FIG. 4, during operation, via the electrosurgical generator 101 (see FIG. 4), of the electrosurgical instrument performing the ablation, conductivity, which is the inverse of impedance, is measured (via one or more sensor modules 110) to provide tissue properties and the degree of hydration and motility of water in the tissue. The first derivative of the conductivity is calculated by the outer loop control module 404 to establish a setpoint value to be communicated to the inner loop control module 402 to control the electrosurgical generator 101. The maxima and minima of the conductivity/impedance curve can be determined by setting the first derivative of the impedance "Z" as a function of time equal to zero, i.e., "dZ/dt=0" control of the impedance "Z" enables control of the hydration level in the tissue and enables also taking advantage of times in which the reflection coefficient is of a sufficient magnitude to facilitate and enhance tissue division and tissue destruction, when the latter is desired. Conversely, control of the hydration level in the tissue enables proper control of the impedance "Z".

Thus, controlling the application of electrosurgical energy to the surgical site optimizes energy delivery based on the hydration level and/or the water motility and/or the reflection coefficient in the tissue at the surgical site. The electrosurgical energy applied to the surgical site is a function of the hydration level and/or water motility which in turn are identified via specific portions of the readings of maxima and minima of tissue impedance readings.

It should be noted that detecting the generally modified "V-shape" and "W-shape" parameters does not necessarily require modifying the impedance trace that is illustrated in FIG. 5 prior to the increased application of energy exhibited by dashed lines 528₁ and 528₂. However, additional filtering or processing of the impedance trace may enhance detection of the "W-shape" parameters by detailed data analysis performed by the processor software.

At least one property sensed during the post-surgical condition may be indicative of the quality of a tissue seal formed during the surgical procedure. In one embodiment, the sensor module 110 includes a light detector for detecting light generated by a light source and transmitted through (or reflected from) the tissue proximate the surgical site. A proximity sensor having sensing elements placed at opposite surfaces of the tissue may also be included for sensing the distance between the elements which is indicative of the tissue thickness.

From the foregoing description and referring again to FIGS. 1-5, it can be appreciated that the present disclosure relates to a method for performing an electrosurgical procedure at a surgical site on a patient. Referring particularly to FIG. 3, the method includes the steps of continually sensing electrical and physical properties proximate the surgical site, i.e., steps 302 and 304, in which the step of continually sensing properties includes: acquiring readings of tissue electrical impedance with respect to time at the surgical site; identifying the minima and maxima of the impedance readings with respect to time; and correlating at least one of the minima and the maxima of the impedance readings with at least one of hydration level and hydraulic conductivity in the tissue at the surgical site, i.e., steps 304 and 306. The method also includes controlling the application of electrosurgical energy to the surgical site to vary energy delivery based on the step of correlating at least one of the minima and the maxima of the impedance readings with at least one of the hydration level and the hydraulic conductivity in the tissue at the surgical site, i.e., step 306. Those skilled in the art will recognize that the foregoing steps may be implemented by the closed loop control system 100 for use with electrosurgical generator 101 (see FIGS. 1, 2 and 4).

As explained above with respect to FIG. 4, the method may include the step of calculating the inverse of the tissue electrical impedance Z readings to determine readings of tissue electrical conductivity. The step of varying pulse parameters is performed by controlling at least one of the hydration level and water motility by controlling tissue conductivity levels.

As illustrated in FIG. 5, the electrosurgical procedure is an ablation process. The step of correlating at least one of the minima and the maxima of the impedance readings with at least one of hydration level and hydraulic conductivity in the tissue at the surgical site is performed by identifying at least one minimum, e.g., minimum 504c, that is preceded by a change in slope, e.g., the interval between first and second curvature change points 508₁ and 508₂, respectively, representing a decrease in the rate of descent of impedance from a prior maximum, e.g., maximum 502b, to the next minimum, e.g., minimum 504c, forming thereby at least one generally modified V-shaped plot, e.g., generally modified V-shaped plot 524₁, indicative of a change in slope in the V-shape.

In one embodiment, step 306 of correlating at least one of the minima and the maxima of the impedance readings with at least one of hydration level and hydraulic conductivity in the tissue at the surgical site may be performed by identifying at least one maximum that is formed of a low impedance peak, e.g., maximum 514, between two blunt minima, e.g., first blunt minimum 514a and second blunt minimum 514b, to form at least one generally W-shaped plot 526₁.

In one embodiment, step 306 of correlating at least one of the minima and the maxima of the impedance readings with at least one of hydration level and hydraulic conductivity in the tissue at the surgical site may also be performed by identifying at least one minimum, e.g., minimum 504c, that is preceded by a change in slope, e.g., the interval between first and second curvature change points 508₁ and 508₂, respectively, representing a decrease in the rate of descent of impedance from a prior maximum, e.g., maximum 502b, to the next minimum, e.g., minimum 504c, forming thereby at least one generally modified V-shaped plot, e.g., generally modified V-shaped plot 5241, indicative of a change in slope in the V-shape and by identifying at least one maximum that is formed of a low impedance peak, e.g., maximum 514, between two blunt minima, e.g., first blunt minimum 514a and second blunt minimum 514b, to form at least one generally W-shaped plot 5261.

Additionally, the method may further include the step of concluding that the occurrence of the at least one generally W-shaped plot, e.g., W-shaped plot 5261, represents a time period of high Water motility in the patient tissue as compared to the at least one generally modified V-shaped plot, e.g., generally modified V-shaped plot 5241.

Also, the method may further include the step of concluding that the occurrence of the at least one generally modified V-shaped plot, e.g., generally modified V-shaped plot 5241, represents a time period wherein there is low hydraulic conductivity of water in the tissue at the surgical site as compared to the time period of the at least one generally W-shaped plot, e.g., W-shaped plot 5261.

The method may further include the step of comparing the difference in impedance between at least one low impedance peak, e.g., peak 514, to the impedance of the corresponding two blunt minima, e.g., blunt minima 514a and 514b, of at least one generally W-shaped plot, e.g., W-shaped plot 5261, to the difference in impedance between at least one low impedance peak, e.g., peak 518, to the impedance of the corresponding two blunt minima, e.g., blunt minima 518a and 518b, of at least another generally W-shaped plot, e.g., W-shaped plot 5262.

The method may further include the step of concluding that the time period of the at least one generally W-shaped plot, e.g., W-shaped plot 5261, represents a time of high motility of water in the tissue as compared to the time period of the at least another generally W-shaped plot, e.g., W-shaped plot 5262.

The surgeon may implement the method by decreasing application of electrosurgical energy to the surgical site upon identifying the at least one generally modified V-shaped plot, e.g., V-shaped plot 5241 or 5242 or 5243. The surgeon may also implement the method by increasing application of electrosurgical energy to the surgical site to a level sufficient to initiate tissue division upon identifying the at least one generally W-shaped plot, e.g. W-shaped plot 5261, such that the impedance Z increases along the dashed line 5281 to a level at maximum 502f' that is greater than the impedance of the tissue at sixth maximum 502f so as to be sufficient to cause tissue division, e.g., step 308 of FIG. 3.

As discussed above, In lieu of increasing the energy from the electrosurgical generator 101 upon achieving sixth maximum 502f, in order to verify that a time period of relatively high tissue hydration has occurred, the surgeon may instead choose to continue along the curve 500 by terminating the energy at sixth maximum 502f to allow the tissue impedance Z to decrease to approach first blunt minimum 518a followed by a low impedance peak 518 at which the energy is again applied and the impedance decreases for a brief period until a second blunt minimum 518b is formed.

In lieu of terminating the energy at seventh maximum 502g, having confirmed the presence of the first W-shape 5261, the surgeon may manually, or the software controlling the electrosurgical generator 101 is programmed such that, following the occurrence of the second blunt minimum 518b, the energy from the electrosurgical generator 101 is increased such that the impedance Z increases along the dashed line 5282 to a level at maximum 502g' that is greater than the impedance of the tissue at seventh maximum 502g so as to be sufficient to cause tissue division, e.g., step 308 of FIG. 3.

Although this disclosure has been described with respect to various embodiments, it will be readily apparent to those having ordinary skill in the art to which it appertains that changes and modifications may be made thereto without departing from the spirit or scope of the disclosure. For example, it is contemplated that the control module 102 and/or hydration analyzer and controller 102' may include circuitry and other hardware, rather than, or in combination with, programmable instructions executed by a microprocessor for processing the sensed values and determining the control signals to be sent to the power supply 106 and the output stage 104.

While several embodiments of the disclosure have been shown in the drawings, it is not intended that the disclosure be limited thereto, as it is intended that the disclosures be as broad in scope as the art will allow and that the specification be read likewise. Therefore, the above description should not be construed as limiting, but merely as exemplifications of particular embodiments.

What is claimed is:

1. A method for performing an electrosurgical procedure at a surgical site on a patient, the method comprising:
    continually sensing electrical and physical properties proximate the surgical site by:
        acquiring data readings of an electrical impedance of tissue with respect to time at the surgical site;
        identifying portions of the data readings of the electrical impedance of the tissue for minima and maxima; and
        determining a hydration level and a direction of water motility in the tissue at the surgical site;
    controlling application of electrosurgical energy to the tissue at the surgical site to vary one or more parameters of energy delivered based on the hydration level and the direction of water motility in the tissue at the surgical site; and
    terminating application of electrosurgical energy at a first minimum of the electrical impedance of the tissue.

2. The method of claim 1, further comprising:
    calculating the inverse of the data readings of the electrical impedance of the tissue to determine data readings of an electrical conductivity of the tissue.

3. The method of claim 1, wherein the controlling application of the electrosurgical energy includes varying pulse parameters based on either one or both of the hydration level and the direction of water motility by sensing tissue conductivity levels.

4. The method of claim 1, wherein the electrosurgical procedure is an ablation process, and wherein the identifying further includes:
    identifying at least one minimum of electrical impedance of the tissue that is preceded by a change in slope representing a decrease in a rate of descent of the electrical impedance from a prior maximum of electrical impedance of the tissue to the at least one minimum of electrical impedance of the tissue forming thereby at least one generally modified V-shaped plot.

5. The method of claim 4, further comprising:
    decreasing the application of electrosurgical energy to the tissue at the surgical site upon identifying the at least one generally modified V-shaped plot.

6. The method of claim 1, wherein the electrosurgical procedure is an ablation process, and wherein the identifying further includes:

identifying at least one maximum of electrical impedance of the tissue that is formed of a low impedance peak between a first blunt minimum and a second blunt minimum, wherein the at least one maximum of electrical impedance of the tissue, the first blunt minimum, and the second blunt minimum form at least one generally W-shaped plot.

7. The method of claim 6, further comprising:
increasing the application of electrosurgical energy to the tissue at the surgical site to a level sufficient to initiate tissue division upon identifying the at least one generally W-shaped plot.

8. The method of claim 1, wherein the electrosurgical procedure is an ablation process, and wherein the identifying further includes:
identifying at least one minimum of electrical impedance of the tissue that is preceded by a change in slope representing a decrease in a rate of descent of the electrical impedance of tissue from a prior maximum of electrical impedance of the tissue to the at least one minimum of electrical impedance of the tissue forming thereby at least one generally modified V-shaped plot; and
identifying at least one maximum that is formed of a low impedance peak between a first blunt minimum and a second blunt minimum, wherein the at least one maximum, the first blunt minimum, and the second blunt minimum form at least one generally W-shaped plot.

9. The method of claim 8, further comprising:
concluding that an occurrence of the at least one generally W-shaped plot is indicative of a high water motility in the tissue at the surgical site.

10. The method of claim 8, further comprising:
concluding that an occurrence of the at least one generally modified V-shaped plot is indicative of a low hydraulic conductivity of water in the tissue at the surgical site.

11. A method for performing an electrosurgical procedure at a surgical site on a patient, the method comprising:
continually sensing electrical and physical properties proximate the surgical site by:
acquiring data readings of an electrical impedance of tissue with respect to time at the surgical site;
identifying portions of the data readings of the electrical impedance of the tissue for minima and maxima; and
determining a direction of water motility in the tissue at the surgical site;
terminating application of electrosurgical energy to the tissue based on the portions of the data readings of the electrical impedance of the tissue and reapplying electrosurgical energy after terminating application of electrosurgical energy; and
controlling application of electrosurgical energy to the tissue at the surgical site to vary one or more parameters of energy delivered based on the portions of the data readings for the minima and the maxima of the tissue electrical impedance indicative of the direction of water motility in the tissue at the surgical site.

12. The method of claim 11, further comprising:
continually outputting electrical signals indicative of the hydration level and the direction of water motility in the tissue at the surgical site.

13. The method of claim 12, wherein the controlling of the application of electrosurgical energy to the tissue at the surgical site includes continually receiving electrical signals to determine the hydration level and the direction of water motility in the tissue at the surgical site and varying one or more parameters of energy delivered based on one or more of the electrical signals to determine the hydration level and the direction of water motility in tissue at the surgical site.

14. A method for performing an electrosurgical procedure at a surgical site on a patient, the method comprising:
continually sensing electrical and physical properties proximate the surgical site by:
acquiring data readings of an electrical impedance of tissue with respect to time at the surgical site;
performing either one or both of graphical analysis and numerical analysis to identify portions of the data readings of the electrical impedance of tissue for minima and maxima of the tissue electrical impedance and determining a direction of resistance to water motility in tissue at the surgical site, including either one or both of:
identifying at least one minimum of the electrical impedance of tissue that is preceded by a change in slope representing a decrease in a rate of descent of the electrical impedance from a prior maximum of the electrical impedance of tissue to the at least one minimum forming thereby at least one generally modified V-shaped plot to determine a low motility of water in the tissue at the surgical site; and
identifying at least one maximum of the electrical impedance of tissue that is formed of a low impedance peak between a first blunt minimum and a second blunt minimum, wherein the at least one maximum of the electrical impedance of tissue, the first blunt minimum, and the second blunt minimum form at least one generally W-shaped plot to determine a high motility of water in the tissue at the surgical site; and
controlling application of electrosurgical energy to the tissue at the surgical site to vary one or more parameters of energy delivered based on the direction of resistance to water motility in the tissue at the surgical site including terminating application of electrosurgical energy in response to reaching a minimum of the electrical impedance of the tissue and reapplying application of electrosurgical energy in response to a maximum of the electrical impedance of the tissue.

* * * * *